United States Patent [19]

Vidakovic et al.

[11] Patent Number: 6,127,140
[45] Date of Patent: Oct. 3, 2000

[54] ASSAY FOR QUANTITATIVE MEASUREMENT OF ANALYTES IN BIOLOGICAL SAMPLES

[75] Inventors: Momcilo S. Vidakovic, Waukegan; David C. Leahy, Grayslake, both of Ill.; Donna M. Massie, Kenosha, Wis.

[73] Assignee: Abbott Laboratories, Abbott Park, Ill.

[21] Appl. No.: 09/335,584

[22] Filed: Jun. 18, 1999

[51] Int. Cl.[7] .............. C12Q 1/26; C12Q 1/54; C12Q 1/40; G01N 33/53

[52] U.S. Cl. .............. 435/25; 435/14; 435/968; 435/11; 435/22; 552/502; 436/71; 568/303

[58] Field of Search .............. 435/25, 14, 968, 435/11, 22; 552/502; 436/71; 568/303

[56] References Cited

U.S. PATENT DOCUMENTS

| | | |
|---|---|---|
| 4,278,760 | 7/1981 | Wulff et al. .............. 435/25 |
| 4,318,980 | 3/1982 | Boguslaski et al. .............. 435/25 |
| 4,380,580 | 4/1983 | Boguslaski et al. .............. 435/25 |
| 4,383,031 | 5/1983 | Boguslaski et al. .............. 435/25 |
| 4,447,529 | 5/1984 | Greenquist et al. .............. 435/25 |
| 4,492,751 | 1/1985 | Boguslaski et al. .............. 435/25 |
| 4,629,688 | 12/1986 | Bolguslaski et al. .............. 435/25 |
| 4,650,750 | 3/1987 | Giese .............. 435/25 |
| 4,791,055 | 12/1988 | Boguslaski et al. .............. 435/25 |
| 4,950,613 | 8/1990 | Arnold, Jr. et al. .............. 435/25 |
| 5,141,854 | 8/1992 | Kaufman et al. .............. 435/25 |
| 5,196,302 | 3/1993 | Kidwell et al. .............. 435/25 |
| 5,206,148 | 4/1993 | Imamura et al. .............. 435/25 |
| 5,294,540 | 3/1994 | Daniel et al. .............. 435/25 |
| 5,332,662 | 7/1994 | Ullman .............. 435/25 |
| 5,395,755 | 3/1995 | Thorpe et al. .............. 435/25 |
| 5,416,004 | 5/1995 | Detwiler .............. 435/25 |
| 5,429,931 | 7/1995 | Detwiler et al. .............. 435/25 |
| 5,429,932 | 7/1995 | Detwiler et al. .............. 435/25 |
| 5,445,944 | 8/1995 | Ullman .............. 435/25 |
| 5,525,481 | 6/1996 | Kaufman et al. .............. 435/25 |
| 5,624,813 | 4/1997 | Mahant .............. 435/25 |
| 5,650,270 | 7/1997 | Giese et al. .............. 435/25 |
| 5,795,784 | 8/1998 | Arnquist et al. .............. 435/25 |

FOREIGN PATENT DOCUMENTS

| | | |
|---|---|---|
| 0 330 433 B1 | 8/1989 | European Pat. Off. . |
| 0 464 942 A1 | 1/1992 | European Pat. Off. . |
| 92/12424 | 7/1992 | WIPO . |

OTHER PUBLICATIONS

Hammond, et al., "Nucleophilic Addition to the 9 Position of 9–Phenylcarboxylate–10–methylacridinium Protects against Hydrolysis of the Ester", Journal of Bioluminescence and Chemiluminescence, vol. 6, pp. 35–43 (1991).

P.G. Mattingly, "Chemiluminescent 10–Methyl–Acridinium–9–(N–Sulphonylcarboxamide) Salts. Synthesis and Kinetcis of Light Emission", Journal of Bioluminescence and Chemiluminescence, vol. 6, pp. 107–114 (1991).

Wilchek and Bayer, "Biotin–Containing Reagents", Methods in Enzymology, vol. 184, p. 123 (1990).

Weeks, et al., "Acridinium Esters as High–Specific–Activity Labels in Immunoassay", Clinical Chemistry, vol. 29, No. 8, pp. 1474–1479 (1983).

Primary Examiner—Louise N. Leary
Attorney, Agent, or Firm—David L. Weinstein

[57] ABSTRACT

A method for determining concentration of an analyte in a biological sample comprising the steps of:

(a) combining the biological sample, at least one oxidizing enzyme for the analyte of interest, nicotinamide adenine dinucleotide (hereinafter NAD$^+$), and a chemiluminescent label to form a reaction mixture;

(b) allowing the analyte to undergo an oxidation-reduction reaction and NAD$^+$ to be converted to the reduced form of nicotinamide adenine dinucleotide (hereinafter NADH) and further allowing the chemiluminescent label to react with NADH; and (c) determining the concentration of the analyte of interest in the biological sample by correlating the quantity of light emitted with the concentration of NADH.

28 Claims, 21 Drawing Sheets

*THE HIGHER AMMONIA CONCENTRATION THE HIGHER THE LIGHT OUTPUT SINCE NADH, WHICH DEACTIVATES ACRIDINIUM, IS CONSUMED DURING THE ENZYMATIC CONVERSION OF AMMONIA

ASSAY FOR QUANTITATIVE MEASUREMENT OF ANALYTES IN BIOLOGICAL SAMPLES

BACKGROUND OF THE INVENTION

1. Field of the Invention

This invention involves a method for measuring the quantity of analytes in biological samples, and, more particularly, a method for measuring the quantity of analytes in biological samples by means of deactivation of a chemiluminescent label.

2. Discussion of the Art

Current assays for blood alcohol level are based on reactions catalyzed by two enzymes, yeast alcohol dehydrogenase and diaphorase, followed by attenuation of the light emitted by a fluorophore. These assays are often referred to as "radiative energy attenuation" assays, or REA assays. REA assays involve color development reactions. Their reaction systems use analyte to convert a chromogen (unreacted dye) to a chromophore (colored dye). A stable fluorescent substance (fluorophore) is also included in the reaction mixture. The light-absorbing properties of the chromophore produced cause a decrease of measured fluorescent light intensity from the fluorophore. REA assays are used quantitatively to measure specific analytes based on the principle that the logarithm of measured fluorescent light intensity is inversely proportional to the amount of chromophore present. Production of chromophore is linked by the reaction system to consumption of analyte, so development of fluorescent attenuation can be calibrated to measure the concentration of analyte in the sample. The reactions for determining ethanol concentration in a biological sample can be expressed as follows:

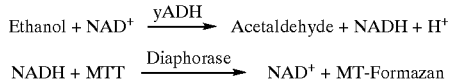

where
- yADH represents yeast alcohol dehydrogenase;
- $NAD^+$ represents nicotinamide adenine dinucleotide;
- NADH represents the reduced form of nicotinamide adenine dinucleotide;
- MTT represents 3-(4,5-dimethylthiazol-2-yl)-2,5-diphenyl-2H-tetrazolium bromide; and
- MT-Formazan represents a light absorbing compound (i. e., a chromophore).

In the foregoing reactions, the reaction product MT-Formazan blocks the transmission of light. The greater the quantity of MT-Formazan formed in the foregoing reaction, the greater is the quantity of ethanol in the sample. The foregoing reactions are employed to determine the concentration of ethanol by means of an assay employing an AxSYM® instrument, commercially available from Abbott Laboratories. The relationship between the concentration of ethanol and the measured fluorescence intensity is established by generating a calibration curve. Ethanol calibrators of known concentration are run and the resulting attenuated fluorescence signal is measured. When an unknown is read, its concentration is calculated from the stored calibration curve. The measurement arrangement for determining the concentration of ethanol is illustrated schematically in FIG. 1.

The quantitative measurement of ethanol in biological samples has so far relied upon the following general methods:

(1) chemical oxidation of ethanol in the presence of various oxidizing agents;

(2) biochemical oxidation of ethanol catalyzed by alcohol dehydrogenase enzymes and subsequent colorimetric measurement of NADH;

(3) biochemical oxidation of ethanol catalyzed by alcohol dehydrogenase enzymes followed by the formation of formazan in the presence of diaphorase; formazan then attenuates the light emitted by a fluorescent compound, which is a reagent critical to the method.

These methods suffer from various disadvantages. Assays employing chemical oxidation of ethanol exhibit low sensitivity and are primarily used to provide a preliminary estimate of alcohol intoxication. Assays employing the second method exhibit fairly low sensitivity as well and are susceptible to interference from other light absorbing substances in a sample. Assays employing the third method require a source of fluorescence and a corresponding detection system. Accordingly, a more robust and cost-effective method for quantitative determination of ethanol in biological samples is needed.

U.S. Pat. No. 4,950,613 discloses a method of preparing a labelled specific binding partner, such as a biological probe in the form of an antibody or oligonucleotide probe, using a protected label (the corresponding unprotected label being susceptible to inactivation, such as by hydrolysis, to yield a non-chemiluminescent form of the label). The specific binding partner is linked to the label, and an adduct of the label is prepared using a protective adduct former, which produces a protected label, which is less susceptible to inactivation. Particularly preferred are the acridiniums and acridans. Formation of the protected label is preferably an equilibrium reaction that is readily reversible, such as by dilution or oxidation of the protective adduct former.

U.S. Pat. No. 5,294,540 discloses a multilayer analytical element for quantitatively assaying ethanol comprising a tetrazolium salt, alcohol dehydrogenase, $NAD^+$, and an electron transfer agent. The layer comprising the electron transfer agent also includes a polymer having recurring negatively charged groups, and the $NAD^+$ is in a different layer.

U.S. Pat. No. 5,624,813 discloses chemiluminescence-based assays that detect or quantify NAD(P)-linked dehydrogenases and oxidoreductases, or the cofactors, or detect or quantify substrates, intermediates or products of reactions catalyzed by these enzymes by coupling the enzyme reactions to luminescence generating systems. The assays include the steps of reacting a peroxidase with the NAD(P)H produced in a reaction catalyzed by an oxidoreductase that requires $NAD(P)^+/NAD(P)H$ as a cofactor; and then adding a chemiluminescent moiety to produce chemiluminescence from which the analyte, such as an amino acid or sugar, the activity of the oxidoreductase or $NAD(P)^+/NAD(P)$ analyte is determined.

Up to now, no assay for ethanol has effectively eliminated or reduced the interference from substances present in the biological sample. An example of such interference is background absorption in colorimetric assays.

SUMMARY OF THE INVENTION

This invention provides a method for determining concentration of an analyte in a biological sample comprising the steps of:

(a) combining the biological sample, at least one oxidizing enzyme for the analyte of interest, nicotinamide adenine dinucleotide (hereinafter $NAD^+$), and a chemiluminescent label to form a reaction mixture;

(b) allowing the analyte to undergo an oxidation-reduction reaction and NAD$^+$ to be converted to the reduced form of nicotinamide adenine dinucleotide (hereinafter NADH) and further allowing the chemiluminescent label to react with NADH; and (c) determining the concentration of the analyte of interest in the biological sample by correlating the quantity of light emitted with the concentration of NADH.

The chemiluminescent label can be introduced at the same time as the biological sample, the oxidizing enzyme and the NAD$^+$, or it can be introduced in a separate step, such as, for example, subsequent to the commencing of the formation of NADH. In the case where ethanol is the analyte of interest, the oxidizing agent is preferably yeast alcohol dehydrogenase.

NADH, the reduced form of nicotinamide adenine dinucleotide coenzyme, is generated during the enzyme-catalyzed conversion of an analyte, e. g., ethanol, to a bio-oxidation product, e. g., acetaldehyde in the case of ethanol. Other analytes can be determined by the method of this invention, but the bio-oxidation products of these analytes may not be acetaldehyde. The reactivity of NADH or analogues of NADH with acridinium derivatives, which provide good chemiluminescent labels, has been studied as a model for enzyme modulated reduction reactions involving transfer of hydride anion. Upon mixing of an acridinium derivative with NADH, NADH rapidly and irreversibly transfers a hydride anion (one proton and two electrons) to the acridinium derivative. The resulting compound, acridan, is averse toward the reaction with alkaline hydrogen peroxide (which is necessary for the chemiluminescent activation of acridinium derivatives), and, consequently, fails to form an intermediate that is critical for the chemiluminescence reaction. Consequently, the amount of acridan formed, the non-chemiluminescent form of the acridinium derivative, is directly proportional to the signal decrease. The signal decrease may be directly correlated to the amount of NADH generated during the stoichiometric conversion of an analyte, e. g., ethanol. Because the conversion of each molecule of the analyte to a corresponding bio-oxidation product requires exactly one molecule of NADH, the signal decrease may be directly correlated to the concentration of the analyte in a biological sample.

Representative examples of analytes that can be detected by the method of this invention include, but are not limited to, ethanol, ethylene glycol, phenytoin, glucose, ketone bodies, triglycerides, cholesterol, lactate, α-amylase, ammonia, malate, androsterone, and testosterone. Preferred analytes include ethanol and ethylene glycol. Representative examples of oxidizing enzymes that can be employed in this method include, but are not limited to, alcohol dehydrogenase, glycerol dehydrogenase, glucose dehydrogenase, β-hydroxybutyrate dehydrogenase, lactate dehydrogenase, glutamate dehydrogenase, cholesterol dehydrogenase, androsterone dehydrogenase, testosterone dehydrogenase, and malate dehydrogenase.

In a preferred embodiment, the method of this invention involves the use of a solid phase to reduce background interference. In the preferred embodiment, the method comprises the steps of:

(a) combining the biological sample, a solid phase, at least one oxidizing enzyme for the analyte of interest, nicotinamide adenine dinucleotide (NAD$^+$), and a chemiluminescent label to form a reaction mixture;

(b) allowing the analyte to undergo an oxidation-reduction reaction and NAD$^+$ to be converted to the reduced form of nicotinamide adenine dinucleotide (NADH)) and further allowing the chemiluminescent label to react with NADH;

(c) separating the chemiluminescent label from the solid phase; and (d) determining the concentration of the analyte in the biological sample by correlating quantity of light emitted with the concentration of NADH.

The chemiluminescent label can be introduced at the same time as the biological sample, the oxidizing enzyme and the NAD$^+$, or it can be introduced in a separate step, such as, for example, subsequent to the commencing of the formation of NADH.

Chemiluminescent labels, in which luminescence is generated by a chemical oxidation step, and bioluminescent labels, where the energy for light emission is produced by an enzyme-substrate reaction are labelling devices suitable for use in this invention. Derivatives of luminol ($C_8H_7N_3O_2$) and acridine ($C_{13}H_9N$) can be used as chemiluminescent labels. The preferred chemiluminescent label is an acridinium derivative. FIG. 2 illustrates the mechanism of deactivation of a chemiluminescent label.

The method proceeds rapidly when the reaction mixture is maintained at a pH equal to or greater than about 9. In order to maintain the pH of the reaction mixture at a level equal to or greater than about 9, a buffer can be used. Tris/Glycine buffer is a suitable buffer for this purpose. Other buffers that are suitable for this invention can be selected on the basis of the buffering range desired, which, in turn, depends upon the activity of the enzyme, which depends upon the pH of the reaction mixture.

The method of this invention preferably employs a pre-trigger to condition the chemiluminescent label in order to make it amenable to reaction with the trigger. The method of this invention preferably employs a trigger in order to cause the chemiluminescent label to react with a nucleophile, thereby allowing the formation of a compound that emits light, e. g., acridone. In the case of a determination of ethanol, the pre-trigger is preferably a mixture of hydrogen ion and hydrogen peroxide and the trigger is preferably hydroxide ion. The hydrogen ion is preferably supplied by nitric acid and the hydroxide ion is preferably supplied by sodium hydroxide.

In a preferred embodiment of the method of this invention, the method comprises the steps of:

(a) combining a biological sample, a solid phase, at least one oxidizing enzyme for the analyte of interest, and NAD$^+$ to form a reaction mixture;

(b) allowing an analyte, e. g., ethanol, to be converted to a bio-oxidation product, e. g., acetaldehyde in the case of ethanol, and NAD$^+$ to be converted to NADH;

(c) adding a chemiluminescent label to the reaction mixture;

(d) allowing the chemiluminescent label to react with NADH and be captured by the solid phase;

(e) washing the reaction mixture;

(f) releasing the chemiluminescent label; and (g) determining the concentration of analyte by correlating quantity of light emitted with the concentration of NADH.

In this embodiment, a preferred solid phase comprises paramagnetic microparticles, preferably made of polystyrene, and having attached thereto a first specific binding member. The first specific binding member specifically binds to a second specific binding member, which is attached to the chemiluminescent label.

Advantages of the method of this invention include reduction or elimination of background interference, increased sensitivity, and reduced cost.

DETAILED DESCRIPTION

Figure 1:
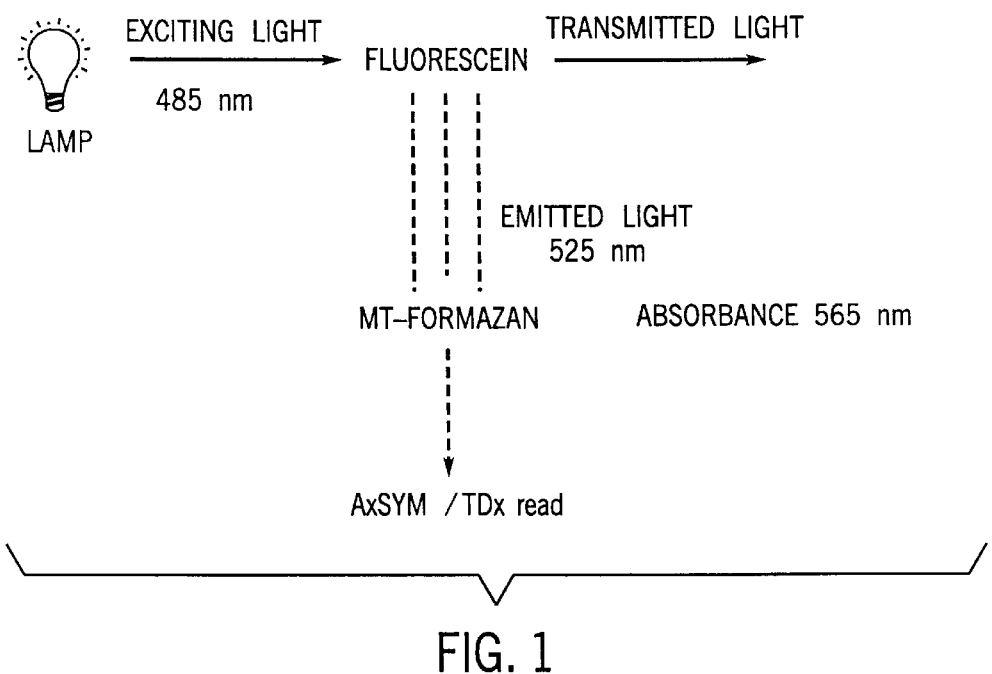
FIG. 1 is a schematic diagram illustrating an arrangement employed in the prior art for determining the concentration of ethanol in a biological sample.

As used herein, the term "chemiluminescent" means the property of a compound that emits light as a result of a chemical reaction at environmental temperature. The term "label" means a group attached to an antibody or an analyte or an analyte analogue to render the reaction between the antibody and the analyte or analyte analogue detectable. Representative examples of labels include enzymes, radioactive labels, fluorophores, and chemicals that produce light. A label is any substance that can be attached to an appropriate molecule and that is capable of producing a signal that is detectable by visual or instrumental means. Various labels include catalysts, enzymes, liposomes, and other vesicles containing signal producing substances such as chromogens, catalysts, fluorescent compounds, chemiluminescent compounds, enzymes and the like. In this invention, the preferred label is a chemiluminescent compound. The term "tracer" is synonymous with the term label. The phrase "solid phase" means a plurality of microparticles having specific binding members chemically or physically bound thereto. Microparticles that can be used in this invention are preferably made of polymeric material, and more preferably include microparticles derived from polymers having styrene units or polymers having acrylate units. The microparticles are preferably substantially spherical and preferably have radii ranging from about 1 $\mu$m to about 10 $\mu$m. A preferred method for separating these microparticles from the test sample involves capture of the microparticles by means of a magnetic field. In this preferred method, the solid phase comprises a mixture of magnetizable microparticles having specific binding members chemically or physically bound thereto. Magnetizable microparticles that are useful in this invention preferably have ferric oxide or chromium oxide cores and a polymeric coating. Such coatings are preferably made from homopolymers and copolymers having styrene units, homopolymers and copolymers having carboxylated styrene units, or homopolymers and copolymers having acrylate or methacrylate units. Other solid phases that are known to those skilled in the art include the walls of wells or reaction trays, tubes, polymeric beads, nitrocellulose strips, membranes and the like.

As used herein, the phrase "DS study" means evaluation of assay performance on the "ARCHITECT" Development System. The "ARCHITECT" Development System is described in U.S. Pat. No. 5,795,784. The term "buffer" means aqueous solution comprising a weak acid and its conjugate base. Buffers resist changes in pH upon addition of small amounts of acid or base. The phrase "trapping agent" means a compound that reacts chemically with the product(s) of an enzyme-catalyzed reaction. These product(s) are removed from the reaction mixture by means of a trapping agent, whereby the enzymatic reaction is driven to its completion. In the case of enzyme-catalyzed reaction of ethanol, the reaction product to be removed is acetaldehyde. The phrase "dose-response ratio" means the correlation between the concentration of the analyte (i. e., substance tested) and the response (i. e., detected signal).

The terms "sample", "biological sample", and the like mean a material suspected of containing the analyte. The test sample can be used directly as obtained from the source or following a pretreatment to modify the character of the sample. The sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The sample can be treated prior to use, such as preparing plasma from blood, diluting viscous fluids, and the like. Methods of treatment can involve filtration, distillation, extraction, concentration, inactivation of interfering components, the addition of reagents, and the like. Other liquid samples besides physiological fluids can be used, such as water, food products, and the like, for the performance of environmental or food production assays. In addition, a solid material suspected of containing the analyte can be used as the sample. In some instances it may be beneficial to modify a solid sample to form a liquid medium or to release the analyte. The phrase "acridinium conjugate" means a substance in which an acridinium derivative is attached to a specific binding member. For example, an acridinium derivative suitable for preparing an acridinium conjugate is a salt of 10-sulfopropyl-acridinium-9-(N-sulfonylcarboxamide); a specific binding member suitable for preparing an acridinium conjugate is biotin. The expression "acridinium derivative" means a substance containing an acridinium group. Acridinium derivatives are described in more detail in P. G. Mattingly, "Chemiluminescent 10-Methyl- Acridinium-9-(N-Sulphonylcarboxamide) Salts. Synthesis and Kinetics of Light Emission", Journal of Bioluminescence and Chemiluminescence, Vol. 6, 107 (1991) and I. Weeks, et al., "Acridinium Esters as High-Specific-activity Labels in Immunoassay", Clin. Chem. 29/8, 1474–1479 (1983), both of which are incorporated herein by reference. The term "pre-trigger" refers to a material that places a chemiluminescent label in condition for reaction with a subsequent reactant. The term "trigger" means a material that causes the chemiluminescent label to react with a nucleophile, thereby allowing the formation of a compound that emits light.

This invention provides a method for determining concentration of an analyte in a biological sample comprising the steps of:

(a) combining the biological sample, at least one oxidizing enzyme for the analyte of interest, nicotinamide adenine dinucleotide (hereinafter $NAD^+$), and a chemiluminescent label to form a reaction mixture;

(b) allowing the analyte to undergo an oxidation-reduction reaction and $NAD^+$ to be converted to the reduced form of nicotinamide adenine dinucleotide (hereinafter NADH) and further allowing the chemiluminescent label to react with NADH; and (c) determining the concentration of the analyte of interest in the biological sample by correlating the quantity of light emitted with the concentration of NADH.

The chemiluminescent label can be introduced at the same time as the biological sample, the oxidizing enzyme and the $NAD^+$, or it can be introduced in a separate step, such as, for example, subsequent to the commencing of the formation of NADH.

Representative examples of analytes whose concentrations can be determined by this method include, but are not limited to, ethanol, ethylene glycol, phenytoin, glucose, ketone bodies, triglycerides, β-hydroxybutyrate, cholesterol, lactate, α-amylase, ammonia, malate, androsterone, ammonia, and testosterone. Preferred analytes include ethanol and ethylene glycol. Representative examples of oxidizing enzymes that can be employed in this method include, but are not limited to, alcohol dehydrogenase, glycerol dehydrogenase, glucose dehydrogenase, β-hydroxybutyrate dehydrogenase, lactate dehydrogenase, glutamate dehydrogenase, cholesterol dehydrogenase, androsterone dehydrogenase, testosterone dehydrogenase, and malate dehydrogenase.

Figure 3A:
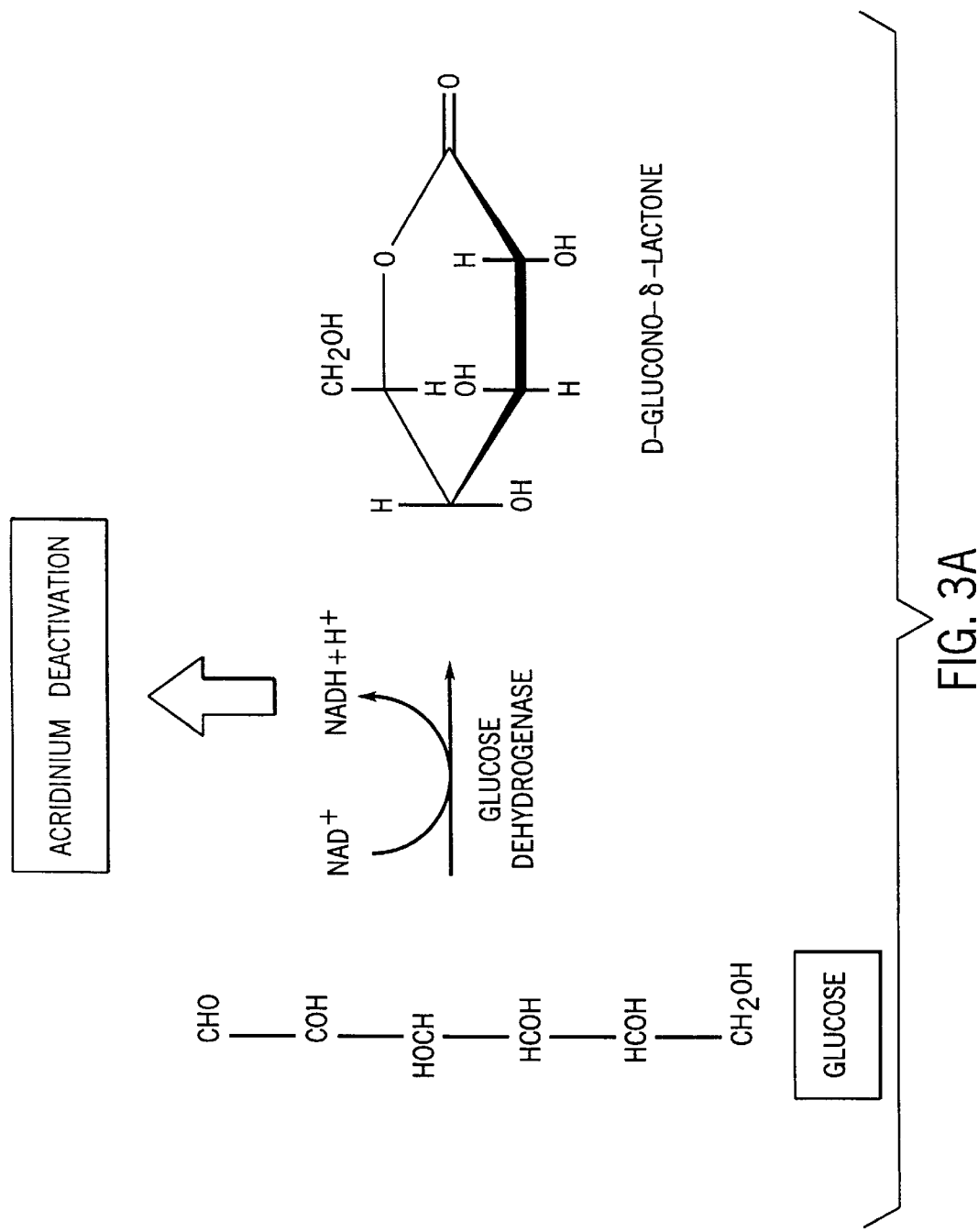
FIGS. 3A, 3B, 3C, 3D, 3E, and 3F are schematic diagrams illustrating the bio-oxidation products of glucose, triglyceride, β-hydroxybutyrate, L-lactate, α-amylase, and ammonia, respectively.
Figure 3B:
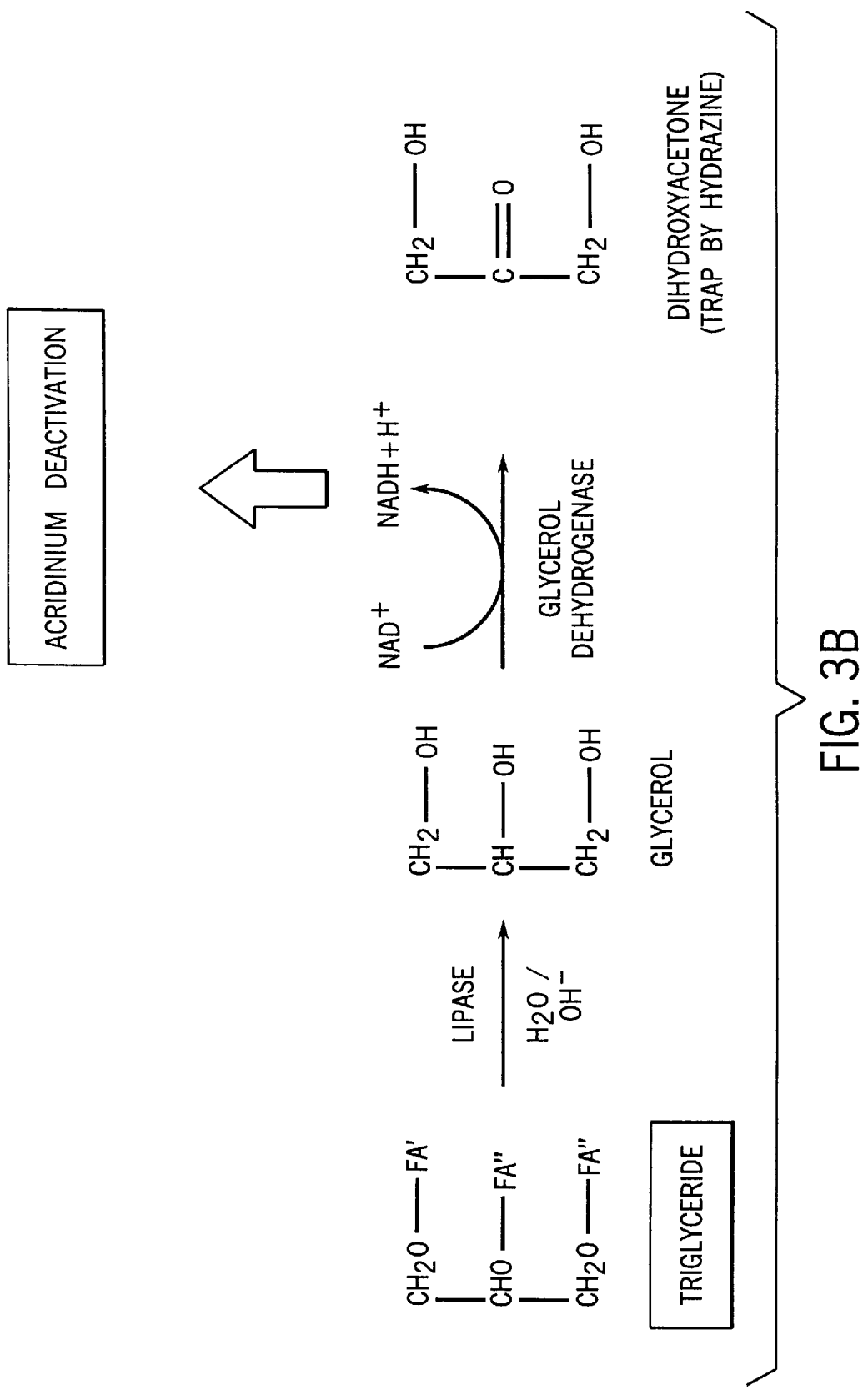
Figure 3C:
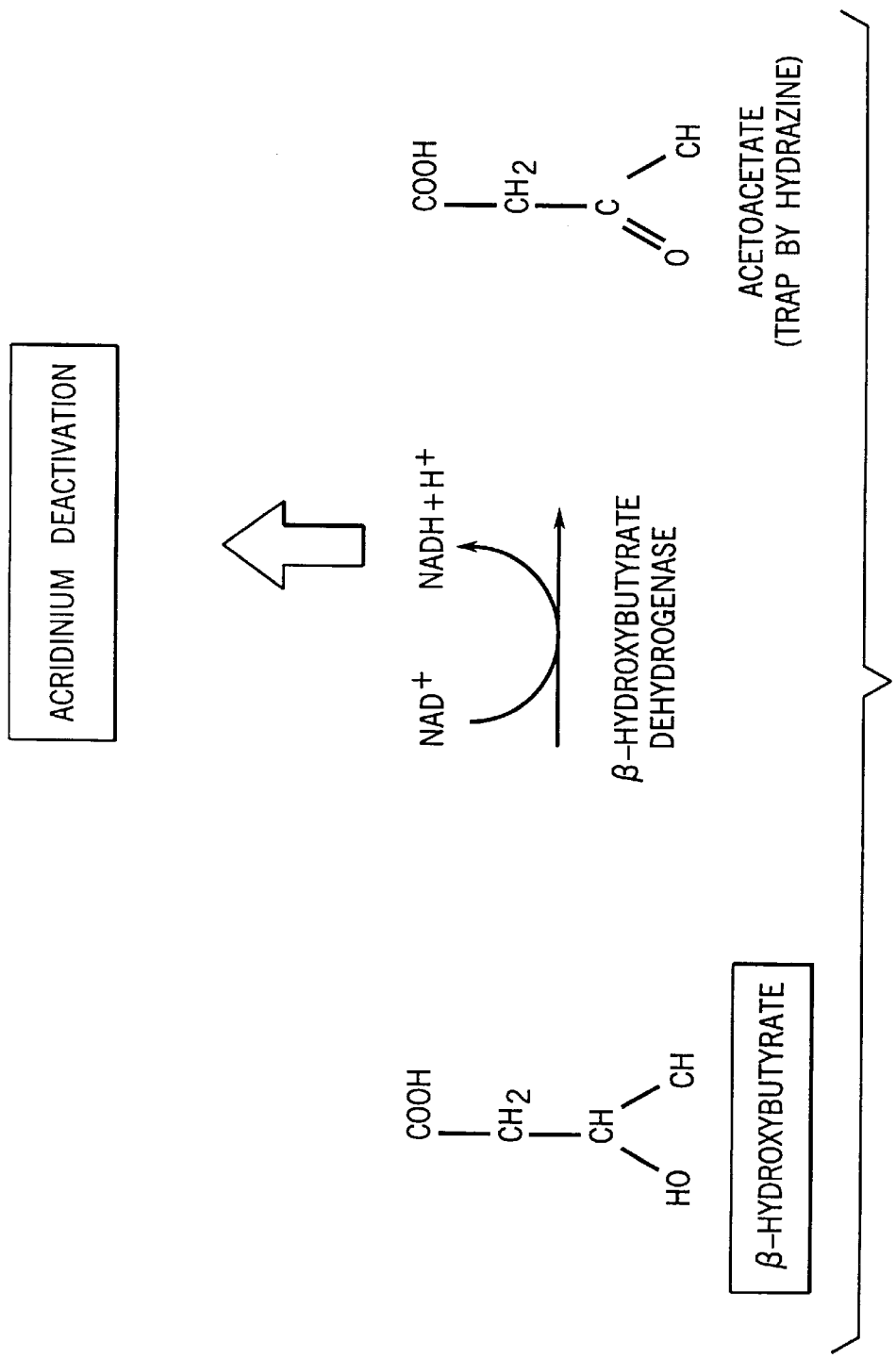
Figure 3D:
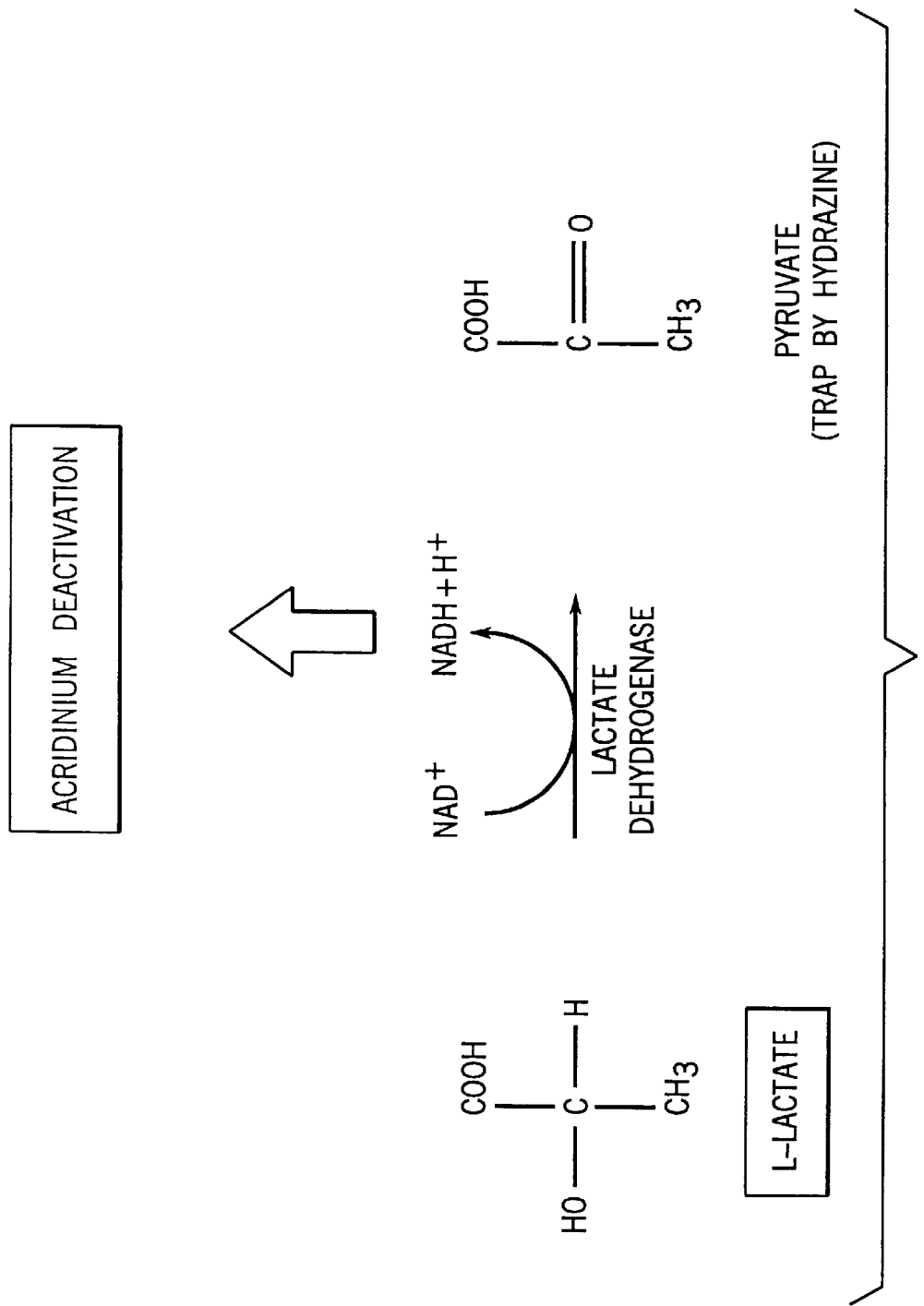
Figure 3E:
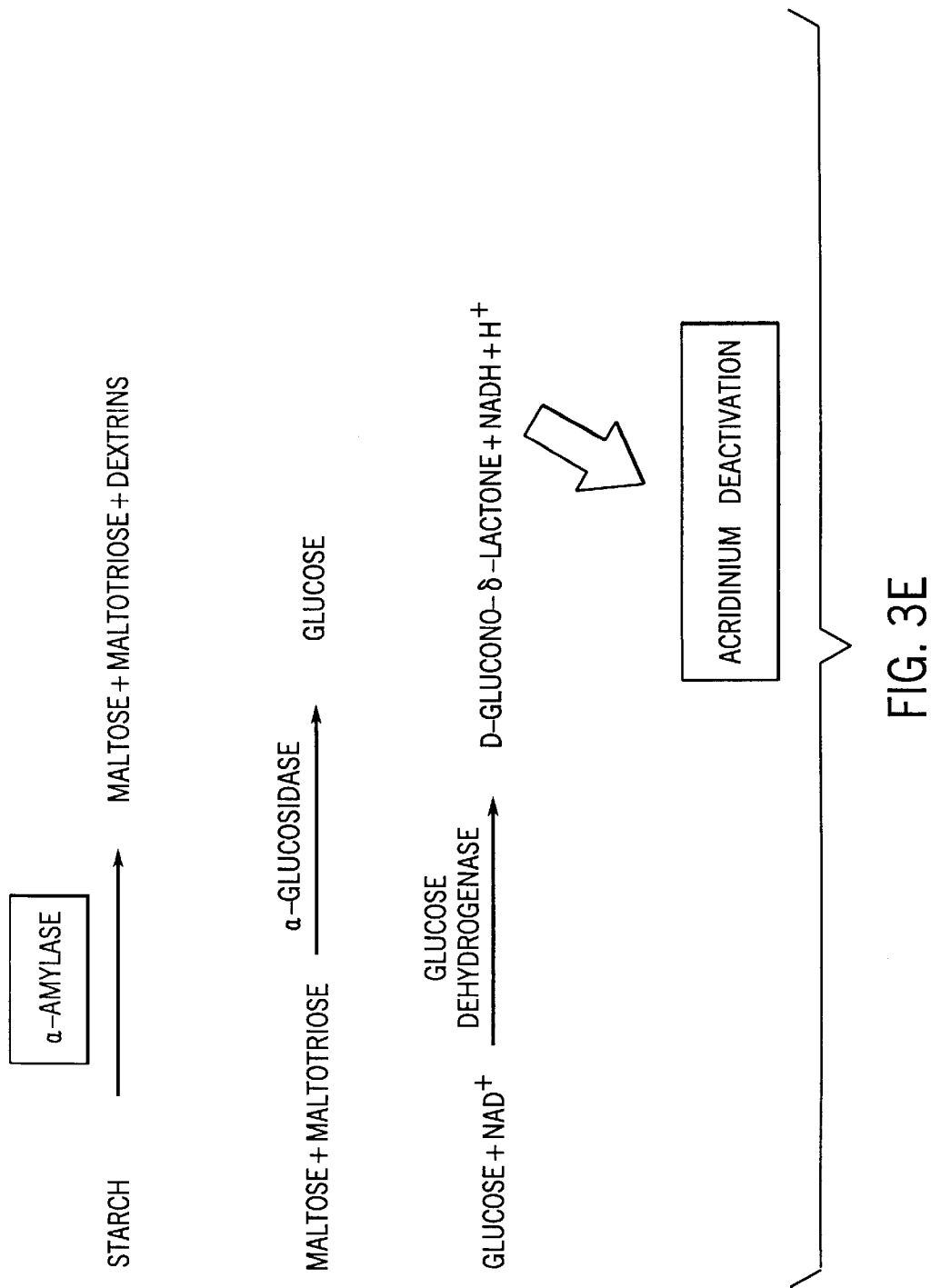
Figure 3F:
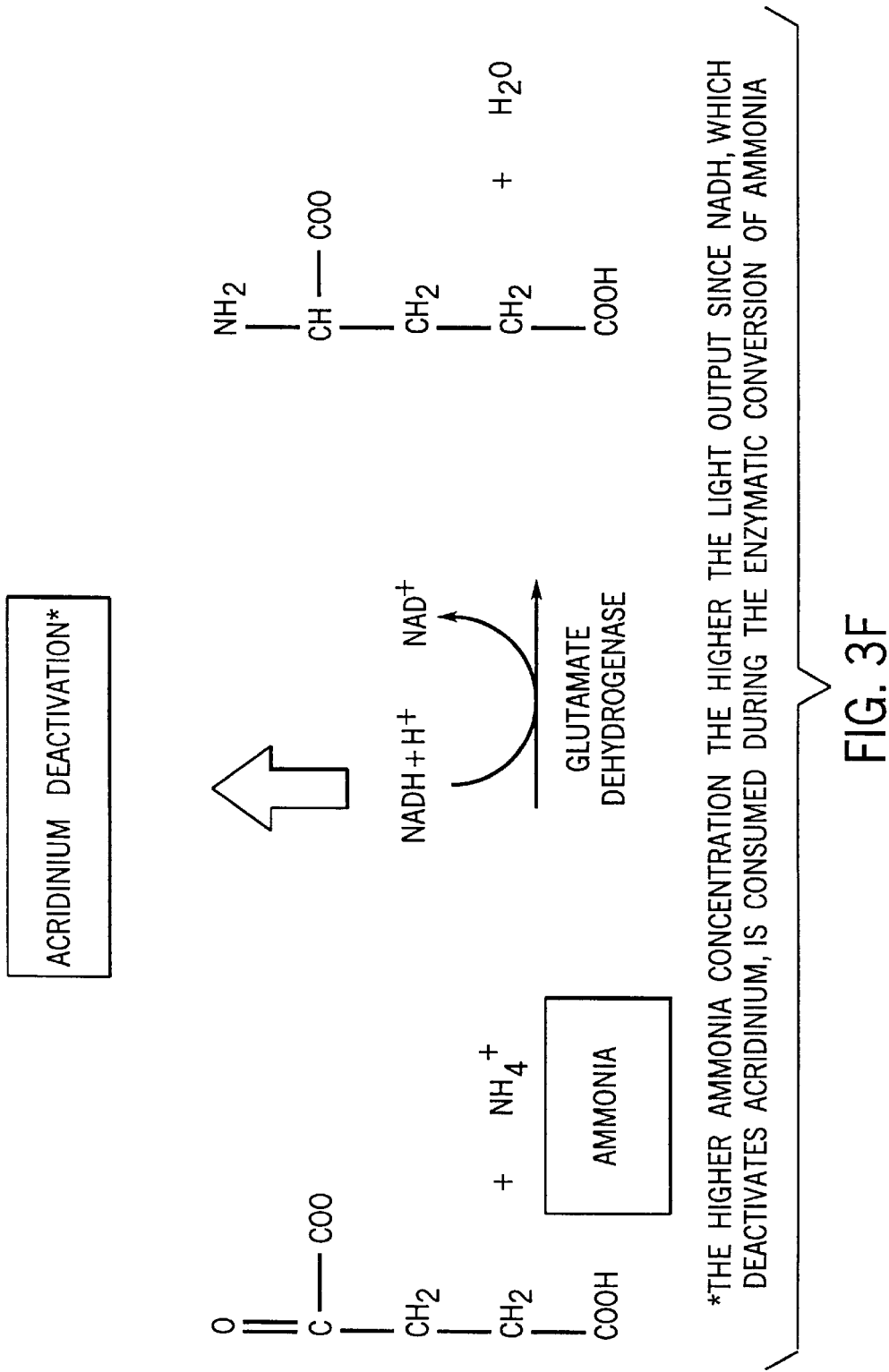

Specific reaction schemes for some of the previously mentioned analytes are set forth in FIGS. 3A–3F for glucose (FIG. 3A), triglyceride (FIG. 3B), β-hydroxybutyrate (FIG. 3C), L-lactate (FIG. 3D), α-amylase (FIG. 3E), ammonia (FIG. 3F).

U.S. Pat. No. 5,795,784, incorporated herein by reference, discloses methods and apparatus for carrying out the determinations of this invention. The preferred embodiment is described in U.S. Pat. No. 5,795,784, in particular, at column 14, line 49 through column 20, line 51.

Figure 4:
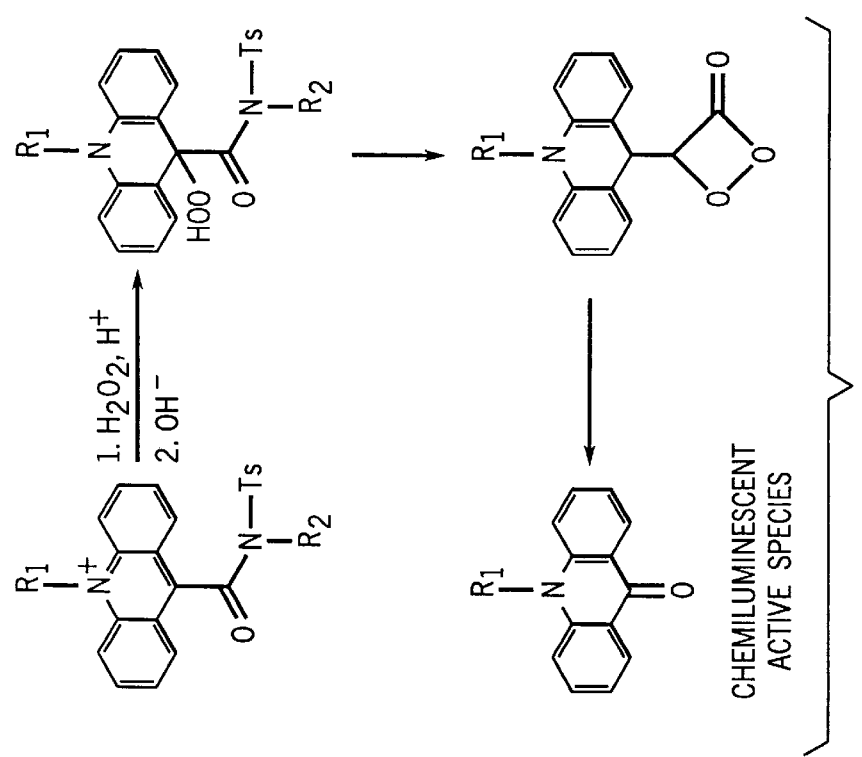
FIGS. 4 illustrates a reaction that results in the formation of the chemiluminescent species of an acridinium derivative.
Figure 5:
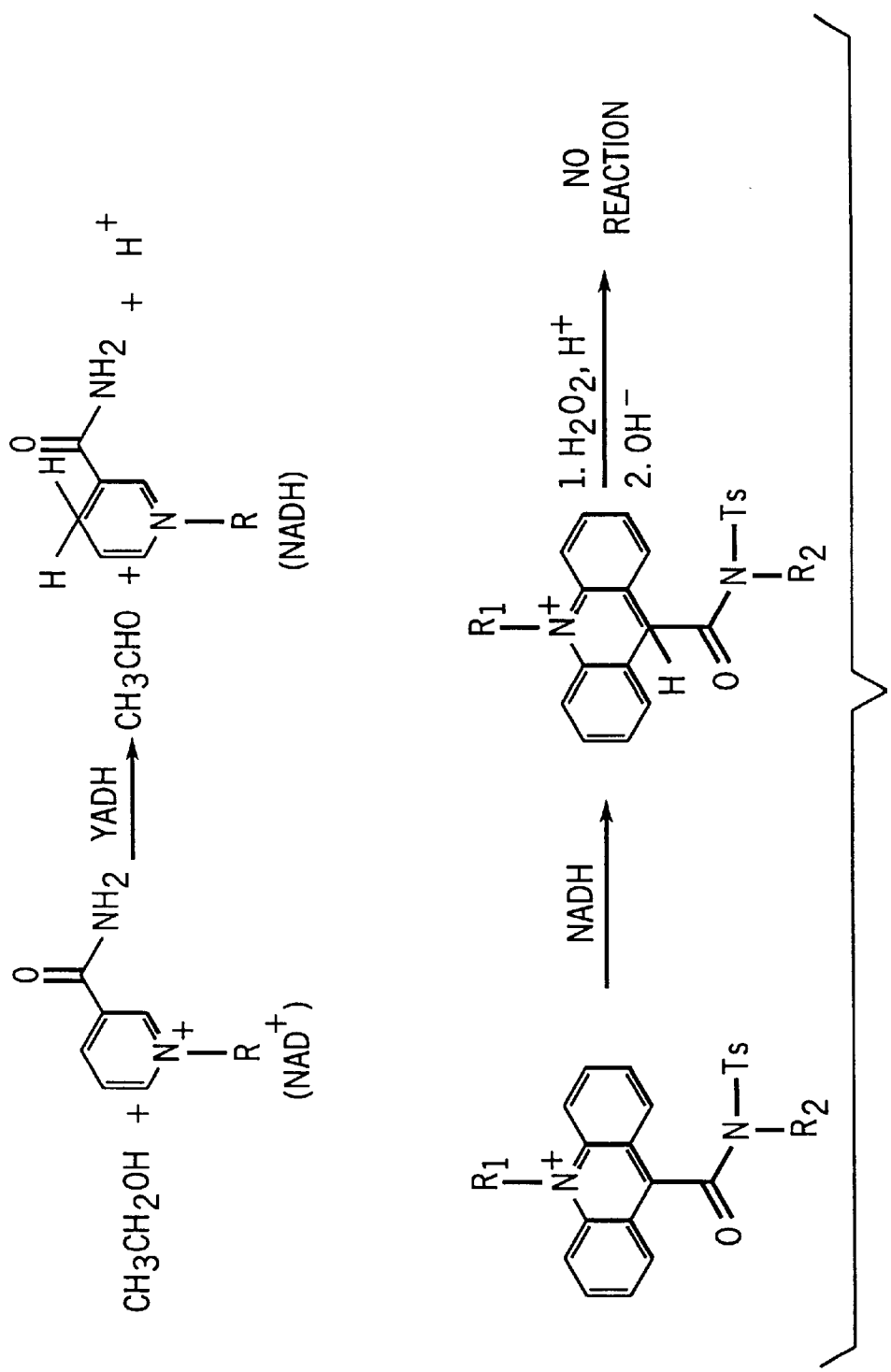
FIG. 5 illustrates a reaction that results in the failure of the formation of a chemiluminescent species of an acridinium derivative.

The assay of this invention is based on the reductive deactivation of a chemiluminescent label, e. g., an acridinium derivative. See FIGS. 4 and 5. FIG. 4 shows a reaction that results in the formation of a chemiluminescent species of an acridinium derivative. FIG. 5 shows a reaction that results in the failure of a chemiluminescent species of an acridinium derivative to form. In FIGS. 4 and 5, the acridinium derivative is 10-sulfopropyl-acridinium-9-(N-sulfonylcarboxamide) wherein $R^1$ represents a sulfopropyl group, $R^2$ represents an n-butyl group, and Ts represents a p-toluenesulfonyl group. The assay utilizes a competitive assay format. When the concentration of the analyte is low, a small population of the label is deactivated, thereby resulting in a relatively high output of light. When the concentration of the analyte is high, a large population of the label is deactivated, thereby resulting in a relatively low output of light.

Figure 6:
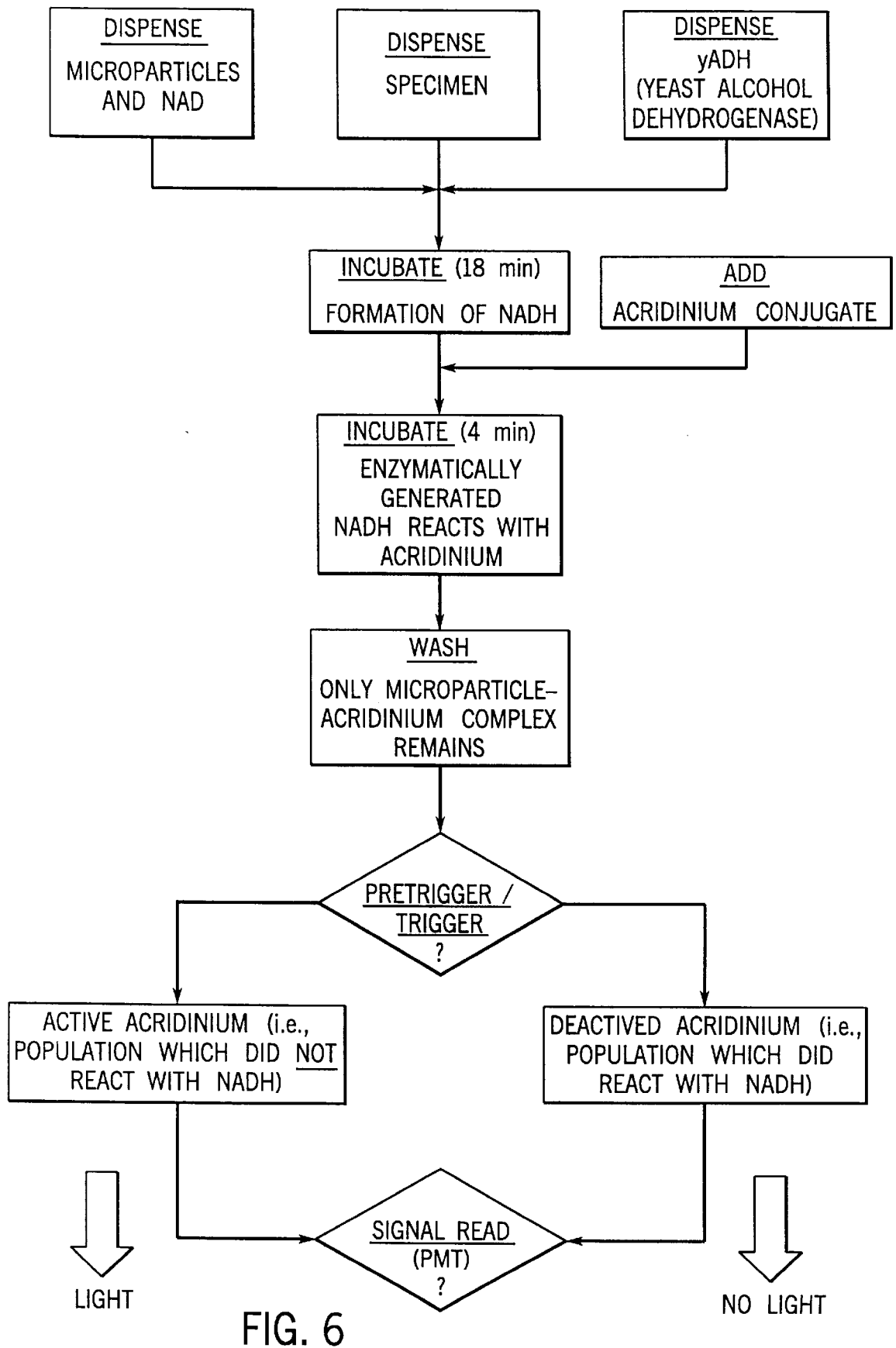
FIG. 6 is a flow chart illustrating an assay for ethanol that can be carried out on the apparatus described in U.S. Pat. No. 5,795,784.

FIG. 6 is a flow chart that shows the steps for carrying out an assay for ethanol by the method of this invention. In the case of analytes other than ethanol, yeast alcohol dehydrogenase is replaced with an appropriate enzyme. In order to conduct the preferred embodiment of the assay, a solid phase, a biological sample, NAD, and yeast alcohol dehydrogenase (yADH) are dispensed into a container. The solid phase is preferably in the form of microparticles having attached thereto a specific binding member. The preferred microparticles comprise polystyrene. The specific binding member attached to the microparticles specifically binds to a specific binding member that is attached to a chemiluminescent label. The specific binding member attached to the microparticles is preferably rabbit monoclonal anti-biotin antibody. The diameter of the microparticles preferably ranges from about 4.0 to about 5.0 µm; the iron content of the microparticles preferably ranges from about 9.5 to about 12.5%; the solid content of the suspension of microparticles in a liquid carrier ranges from about 4.4 to about 5.2%.

Figure 7:
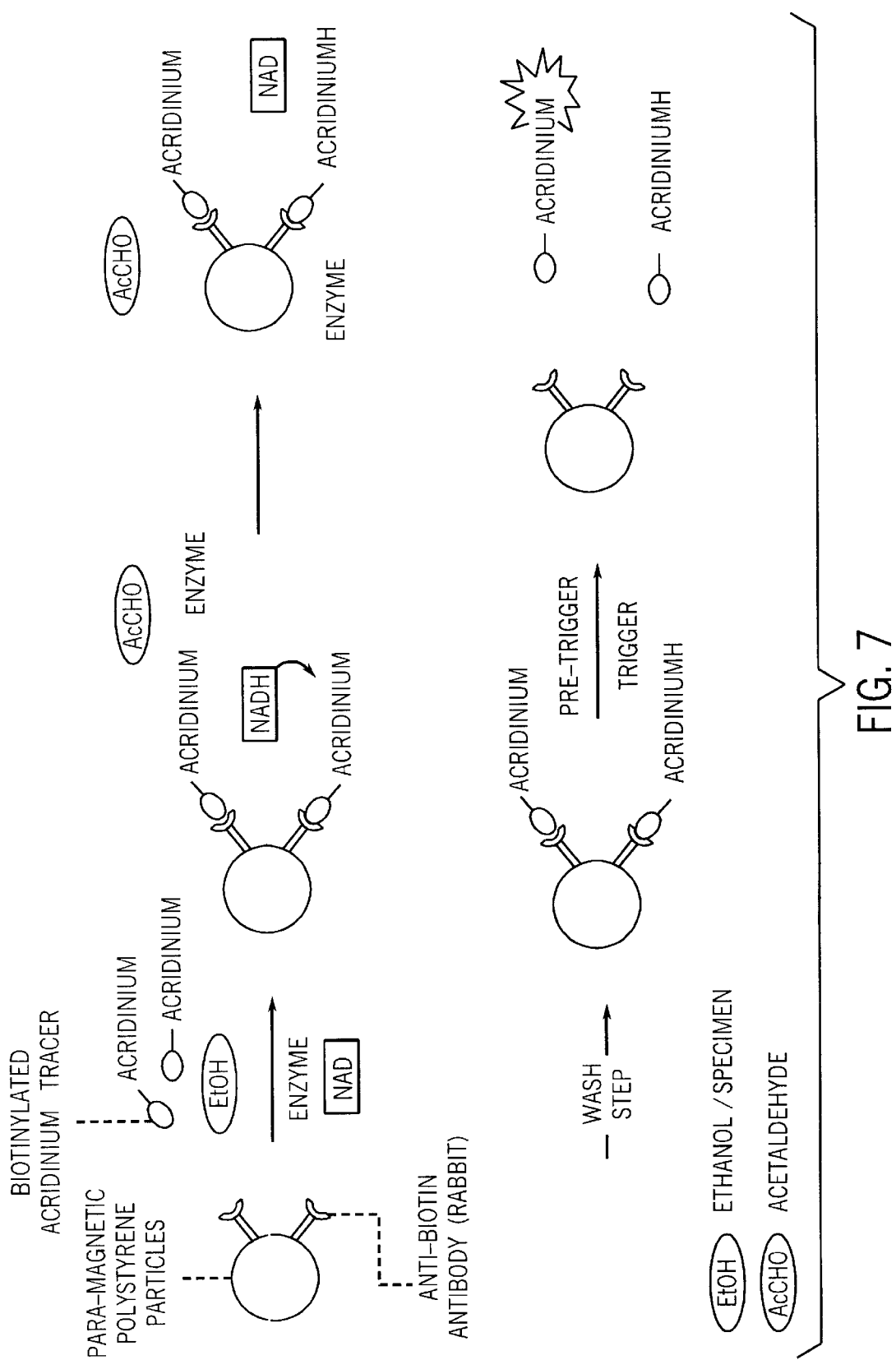
FIG. 7 is a schematic diagram illustrating the reaction scheme for the assay for ethanol.

The resulting mixture is allowed to incubate for a suitable period of time, typically approximately 18 minutes. Then, a conjugate comprising a chemiluminescent label attached to a specific binding member is added to the incubated mixture. The conjugate preferably comprises a biotinylated acridinium derivative. However, other chemiluminescent derivatives can be used instead of acridinium derivatives and other specific binding members can be used instead of biotin. The resulting mixture is then allowed to incubate for a suitable period of time, typically approximately 4 minutes. During this period, the enzymatically generated NADH resulting from the enzymatic conversion of the analyte (ethanol) reacts with the acridinium derivative. The NADH deactivates the acridinium derivative. The mixture is then washed, so that only the complex comprising microparticles and the acridinium derivative remains. The pre-trigger is added to the reaction mixture to condition the chemiluminescent label in order to make it amenable to reaction with the trigger. The pre-trigger preferably comprises a mixture of nitric acid, hydrogen peroxide, and a detergent, e. g., "TRITON X-100" (t-octylphenoxypolyethoxyethanol). The concentration of the nitric acid is preferably 8.3 mmol/L. Then, the trigger is added to the reaction mixture to cause the chemiluminescent label to react with a nucleophile, thereby allowing the formation of a compound that emits light. The trigger preferably comprises sodium hydroxide. The concentration of sodium hydroxide is preferably 0.35 mol/L. The acridinium derivative is activated by alkaline hydrogen peroxide. After the pre-trigger and trigger are added, only the remaining population of active acridinium derivative emits light. FIG. 6 is a flow chart illustrating an assay for ethanol that can be carried out on the apparatus described in U.S. Pat. No. 5,795,784. FIGS. 13, 14, 15, and 16 are flow charts, each of which illustrates an alternate method for carrying out an assay for ethanol. The specific binding member attached to the acridinium derivative binds to antibodies adhered to the surface of the paramagnetic particles. FIG. 7 shows the reaction scheme for the assay for ethanol schematically.

The active acridinium derivative, that is, the population of the acridinium derivative that did not react with NADH, allows emission or generation of light. The deactivated acridinium derivative, that is, the population of the acridinium derivative that did react with NADH, does not emit or generate light. The signal is then read and the measured signal is converted to concentration of analyte.

It should be mentioned that the conjugate can be added to the reaction mixture at any time during the assay. For example, the conjugate can be introduced to the reaction mixture when the biological sample, the oxidizing enzyme, and the solid phase are combined to form a reaction mixture. The conjugate can be introduced to the reaction mixture at a time subsequent to the step of combining the biological sample, the oxidizing enzyme, and the solid phase.

The solid phase can be prepared according to the following procedure:

(a) carboxylated paramagnetic microparticles (4.0 µm particles, 2.5 mL, 5% w/v) are magnetically pelleted; the supernatant is aspirated, and the pellets are washed two times with phosphate buffered saline;

(b) the microparticles are further washed two times with 2-[N-morpholino]ethanesulfonic acid (MES) buffer (5 mL, 50 mM, pH 6.1);

(c) the pellets are resuspended in MES buffer (3.5 mL, 50 mM, pH 6.1); 1-(3-dimethylaminopropyl)-3-ethylcarbodiimide hydrochloride is added (15 mg), and the resulting mixture is mixed for 10 minutes at room temperature;

(d) anti-biotin monoclonal antibody (1.5 mg in MES buffer (1.5 mL, 50 mM, pH 6.1) is then added and the resulting mixture is mixed for 120 minutes at room temperature;

(e) the microparticles are washed five times with phosphate buffered saline to remove any unbound antibody remaining in solution;

(f) the microparticles are resuspended in Tris (2.5% w/v, 50 mM, pH 8.0) containing 100 mM NaCl and 400 mM sucrose;

(g) the microparticles are further diluted to 0.1% w/v in phosphate buffered saline containing 1% bovine serum albumin prior to use.

The acridinium conjugate can be prepared according to the following procedure:

(a) biotin hydrazide is conjugated to acridinium hydroxysuccinimide ester and purified by reverse phase HPLC by means of methods known to one of ordinary skill in the art (see, for example, Methods Enzymol. 1990; 184, 123);

(b) the purified acridinium-biotin label is diluted to 0.2 nmole in 50 mM Tris/Glycine buffer at pH 3.4 prior to use.

The approach of this invention for the quantitative determination of an analyte, e. g., ethanol, involves combining two highly desirable concepts for clinical/biochemical diagnosis of analytes having low molecular weight: (1) rapid enzymatic catalysis and (2) chemiluminescent immunoassays. The design of this assay allows for measurement of the ratio between chemiluminescent and non-chemiluminescent forms of the chemiluminescent label, e. g., an acridinium derivative, which ratio is proportional to the amount of analyte, e. g., ethanol, in the biological sample. Any solid phase required for the preferred format, which includes the wash step, may be eliminated in order to accommodate a homogeneous assay format (i. e., an assay wherein all reagents are in solution). The method of this invention provides the following advantages:

reduced cost plafform flexibility and ease of use accuracy good precision appropriate dynamic range increased sensitivity adaptability to other assays The method of this invention requires only one enzyme for the assay. The AxSYM® ethanol assay (radiative energy attenuation) requires two enzymes. The only enzyme required in the assay for ethanol is yeast alcohol dehydrogenase, an inexpensive reagent. The method of this invention eliminates the cost associated with the second enzyme commonly used in the calorimetric detection method, diaphorase. This single enzyme approach directly affects the chemiluminescent signal measured and is clearly more efficient than the REA type of assay.

The short reaction time of the enzymatic conversion of ethanol and the subsequent deactivation of the chemiluminescent label together with reliable automation of the instrument platform meet numerous requirements concerning both high-throughput and low-throughput laboratory testing. The optional exclusion of a solid phase provides a means for determination of the concentrations of analytes in small laboratories, as well in testing by non-specialists.

Immunoassay technology utilizing a solid phase, e. g., paramagnetic microparticles, allows for thorough washing of the immunochemical complex, which incorporates a modified chemiluminescent label, prior to measurement. The washing steps virtually eliminate endogenous interferences regularly encountered in other assays for ethanol.

Rigorous control of conditions on the automated apparatus (i. e., temperature, mixing of sample and reagents) and good mechanical precision (i. e., volume and velocity of dispensing of reagents and sample) along with rapid deactivation of the acridinium derivative in the presence of NADH provides excellent reproducibility of results.

Chemiluminescent-based detection systems are significantly more sensitive than are colorimetric systems or NADH absorbance measurements. In a chemiluminescent system, there is no interference from background fluorescence or quenching effects, which are common to the other systems. In addition, the nature of a chemiluminescent signal (dark to light generation) along with its superior quantum yield allows for detection of lower levels of analyte. The capability of detecting a lower level of analyte results in an overall increase in dynamic range that can be accurately measured.

The reductive deactivation of a label based on an acridinium derivative relies upon the formation of acridan, a non-chemiluminescent form of acridine. A variety of analytes can be modified in the presence of a suitable dehydrogenase enzyme with the concomitant generation of NADH, which then acts as the antagonist for chemiluminescence of the acridinium derivative. A common antibody attached to a solid phase can then be used to capture chemiluminescent label regardless of the analyte, because the assay measures the ratio of active to deactivated molecules of the acridinium derivative.

The following non-limiting examples will further explain the invention.

EXAMPLES

Example 1

Figure 2:
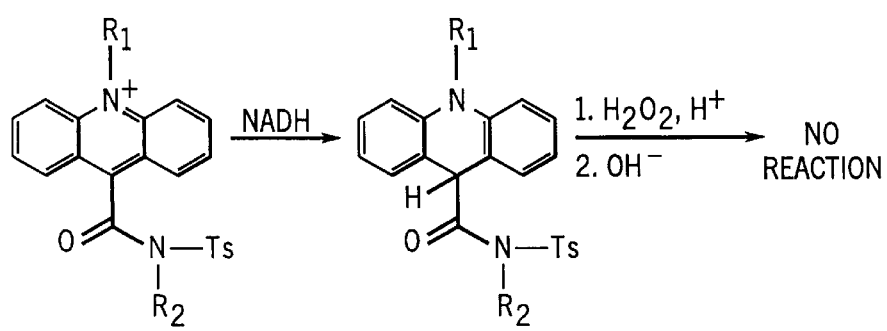
FIG. 2 is a diagram illustrating the reductive deactivation of acridinium derivative.

This example illustrates the characteristics of an acridinium derivative. FIGS. 2, 4, and 5 illustrate chemical reactions characteristic of an acridinium derivative. From FIG. 2, it can be seen that when NADH reacts with the acridinium derivative, there will be no reaction when the reaction product of NADH and the acridinium derivative is further reacted with the pre-trigger ($H_2O_2$, $H^+$) and trigger ($OH^-$).

Example 2

Figure 8:
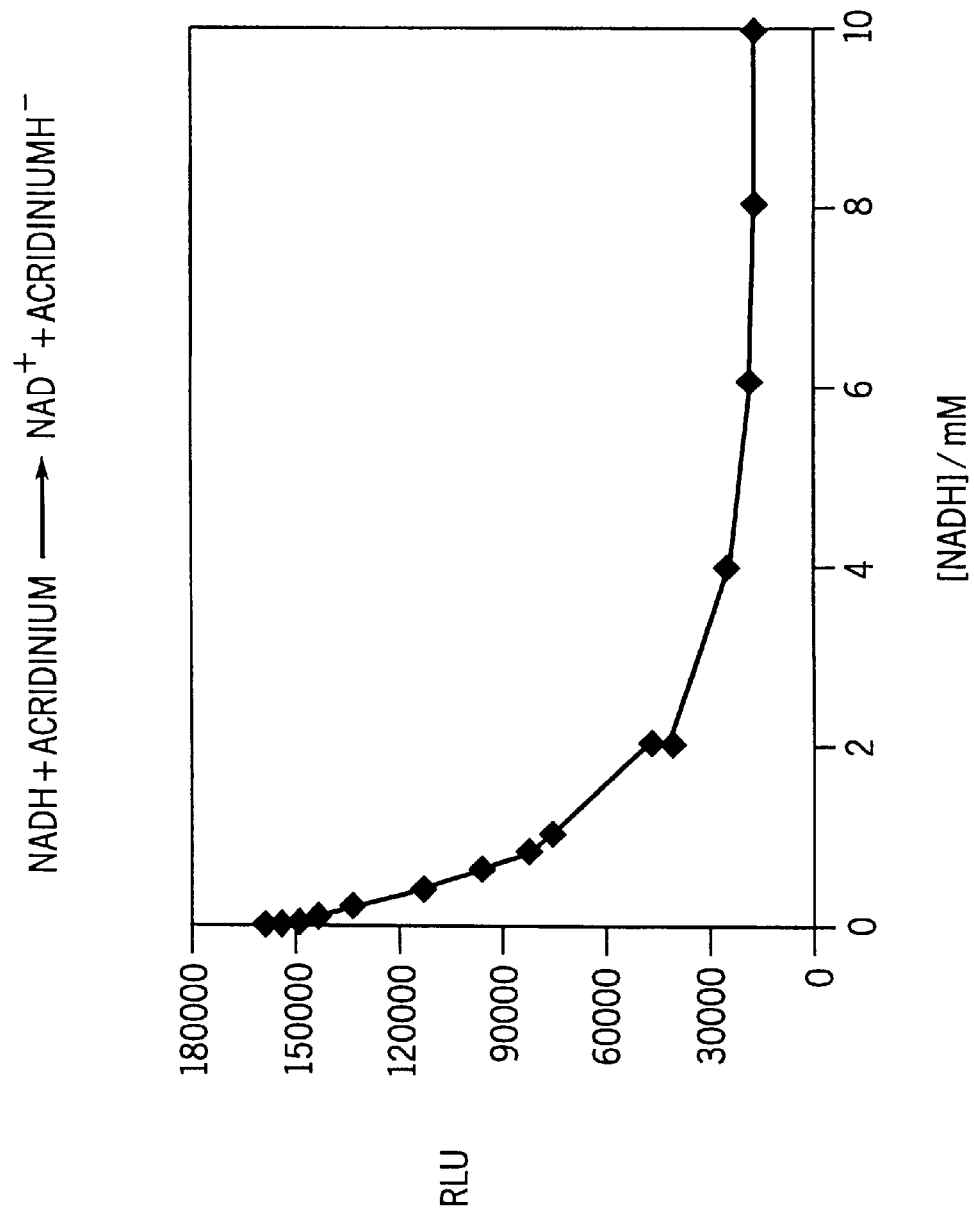
FIG. 8 is a graph illustrating a calibration curve of Relative Light Units (RLU) as a function of concentration of NADH per mM.

This example illustrates a DS study. The purpose of this study was to demonstrate the feasibility of using the reaction of NADH and an acridinium derivative to determine the concentration of an analyte, in this case, ethanol. In this study, the procedure was carried out as shown in FIG. 6, with the following exceptions: (1) no biological sample was used; (2) no NAD$^+$ was used. NADH was incubated with the solid phase for 18 minutes. NADH was then reacted with an acridinium derivative. The incubation time for the mixture containing NADH and the acridinium derivative was four minutes. The remaining steps, i. e., the wash steps, the pre-trigger step, the trigger step, and the read step are the same as those shown in FIG. 6. The results of the study are shown in FIG. 8. The data show that there is a significant decrease in Relative Light Units (RLU) upon incubation of the acridinium derivative with NADH. It can be seen that the calibration curve covers three orders of magnitude with respect to NADH.

Example 3

Figure 9A:
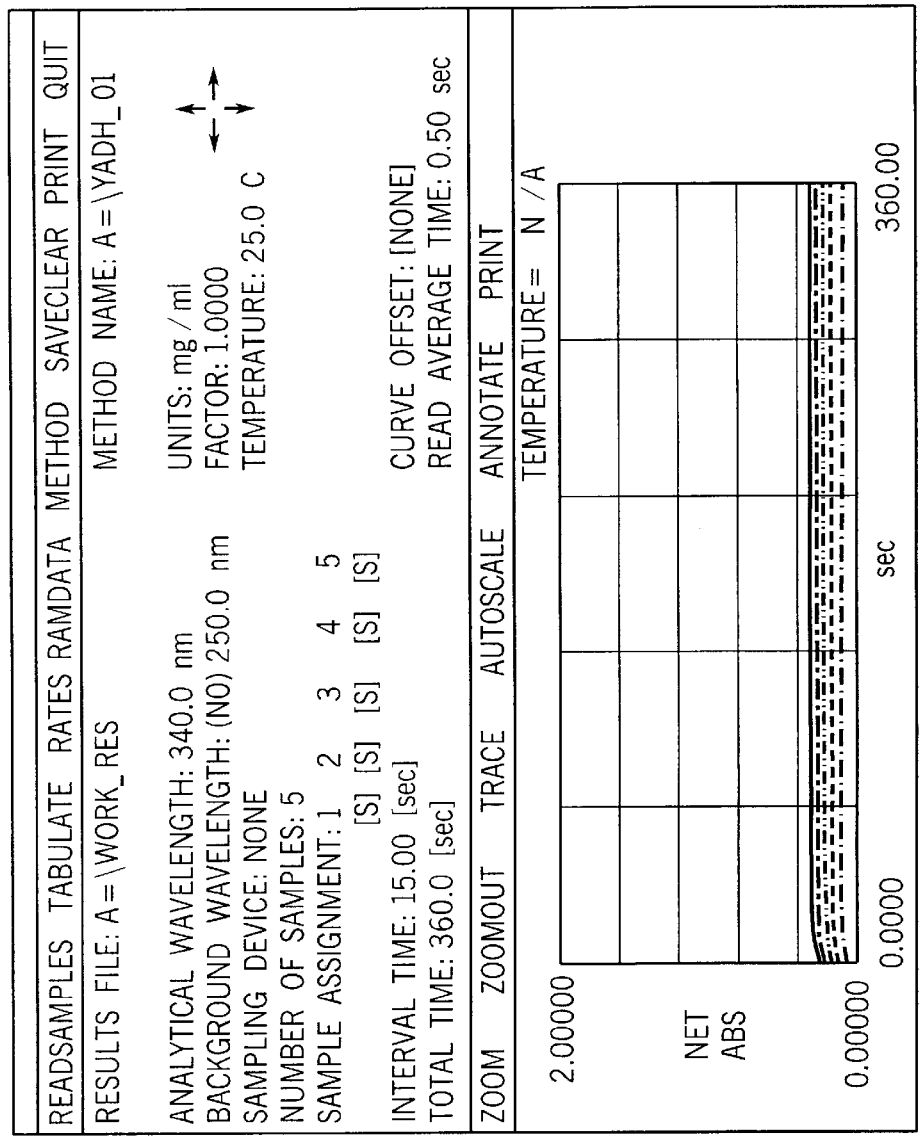
FIGS. 9A and 9B are graphs illustrating the effect of pH and buffer on the conversion of ethanol to acetaldehyde.
Figure 9B:
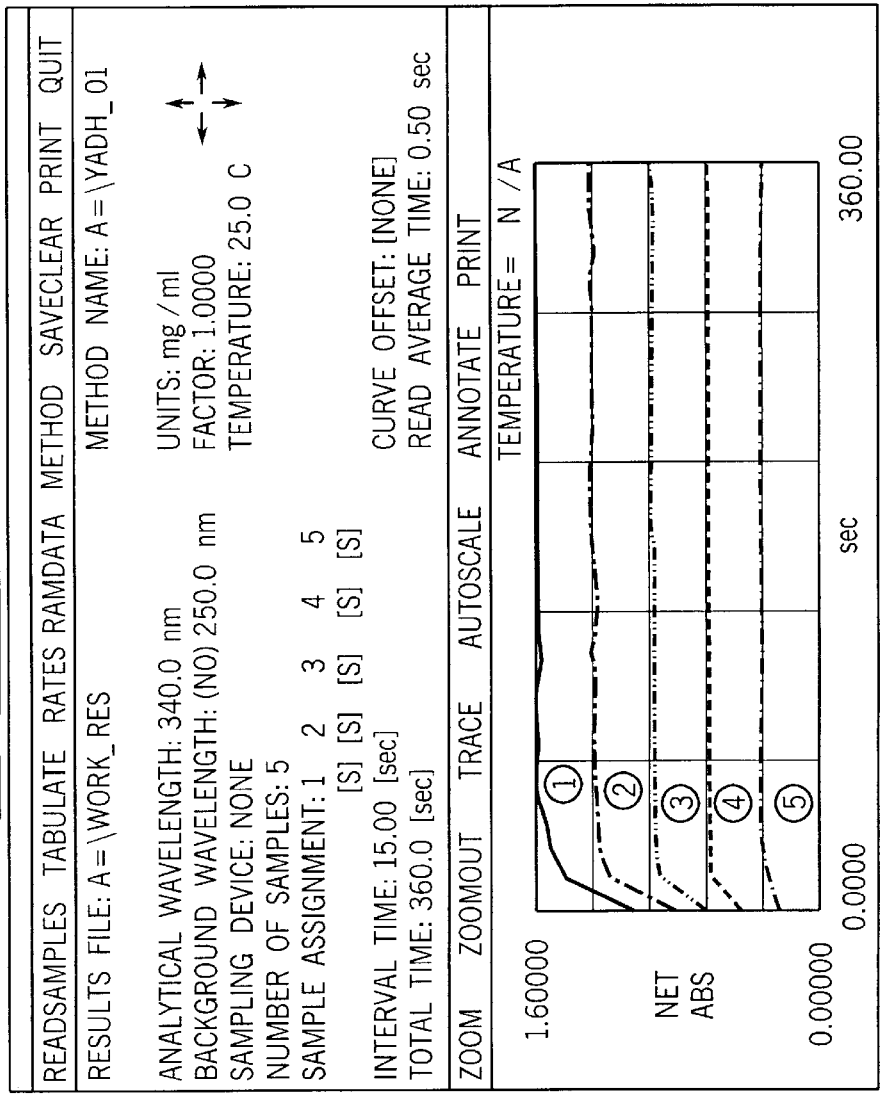
Figure 10:
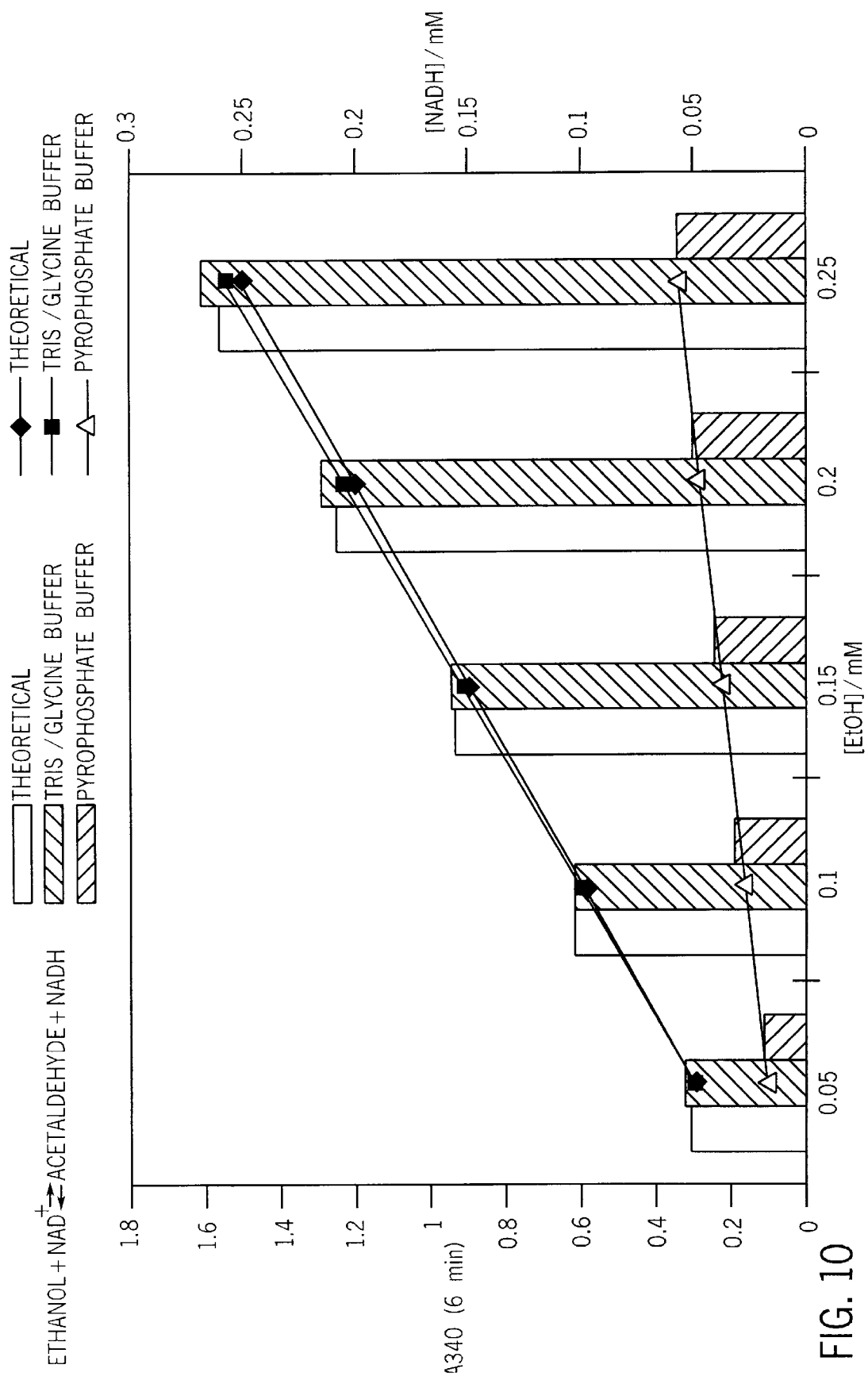
FIG. 10 is graph illustrating the effect of pH and buffer on the conversion of ethanol to acetaldehyde.

This example illustrates the effect of pH of the buffer on conversion of ethanol to acetaldehyde and the effect of trapping agent on conversion of ethanol to acetaldehyde. In this example, ethanol, NAD$^+$, yeast alcohol dehydrogenase, and buffer were combined and the resulting reactions monitored by means of an ultraviolet-visible spectrophotometer. FIG. 9A shows the conversion as a function of time when pyrophosphate buffer having a pH of 8.8 is used. FIG. 9B shows the conversion as a function of time when Tris/Glycine buffer having a pH of 9.6 is used. From the figures, it can be seen that ethanol conversion is slow and incomplete when the pyrophosphate buffer having pH 8.8 is used; it can be seen that ethanol conversion is fast and complete when Tris/Glycine buffer having pH 9.6 is used. Thus, it is preferred that the pH of the buffer be greater than 9. Tris/Glycine buffer also functions as a trapping agent for acetaldehyde. A trapping agent for acetaldehyde is required to drive the reaction toward the formation of NADH. FIG. 10 shows the effect of Tris/Glycine buffer as a trapping agent. The duration of the reaction was less than one minute.

Example 4

Figure 11:
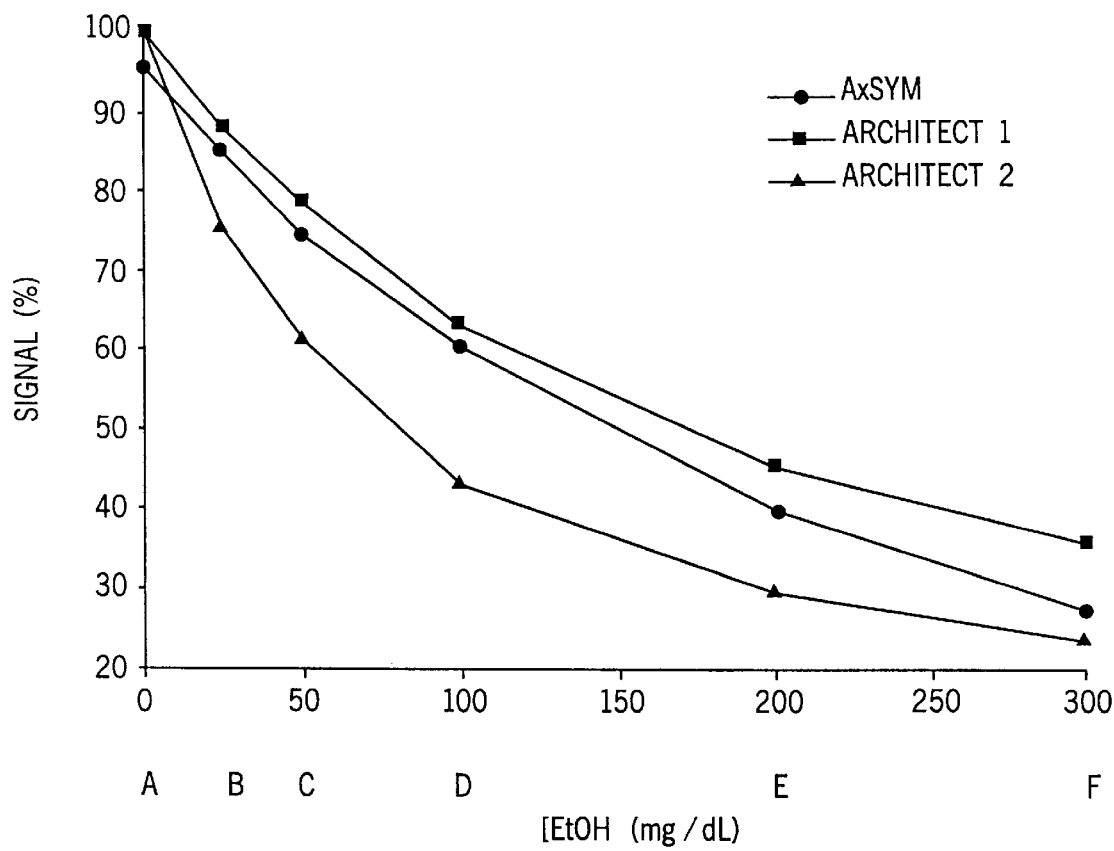
FIG. 11 is a graph comparing the concentration ethanol determined by means of an REA assay with the concentration of ethanol determined by the assay of this invention.
Figure 11:
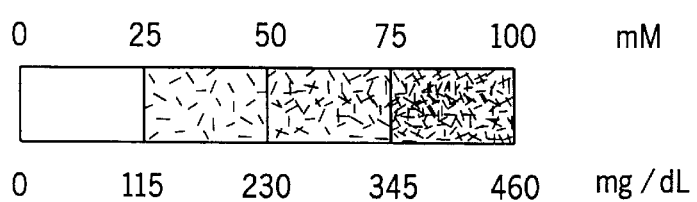
Figure 13:
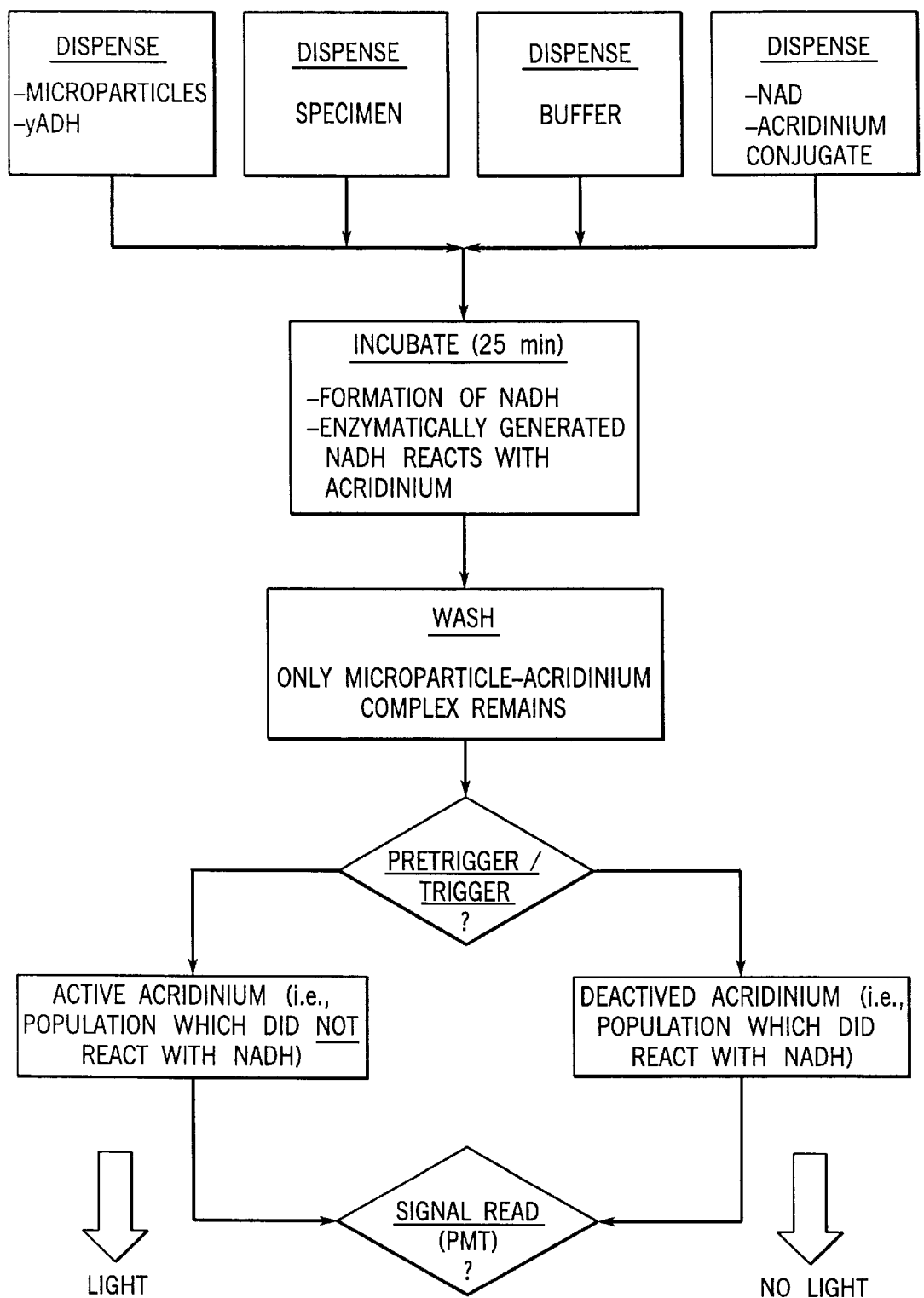
FIG. 13 is a flow chart illustrating an alternate procedure for an assay for ethanol.
Figure 14:
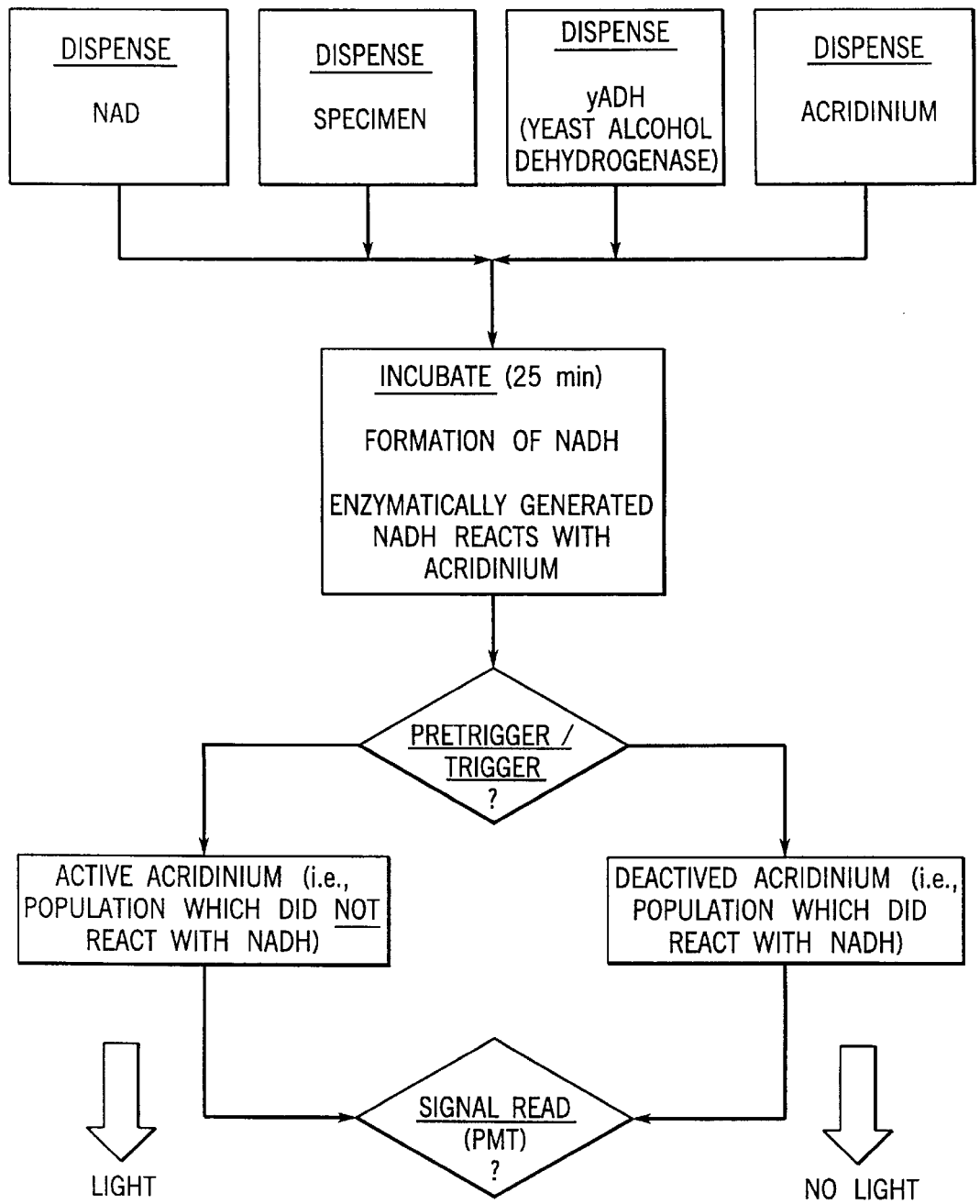
FIG. 14 is a flow chart illustrating an alternate procedure for an assay for ethanol.
Figure 15:
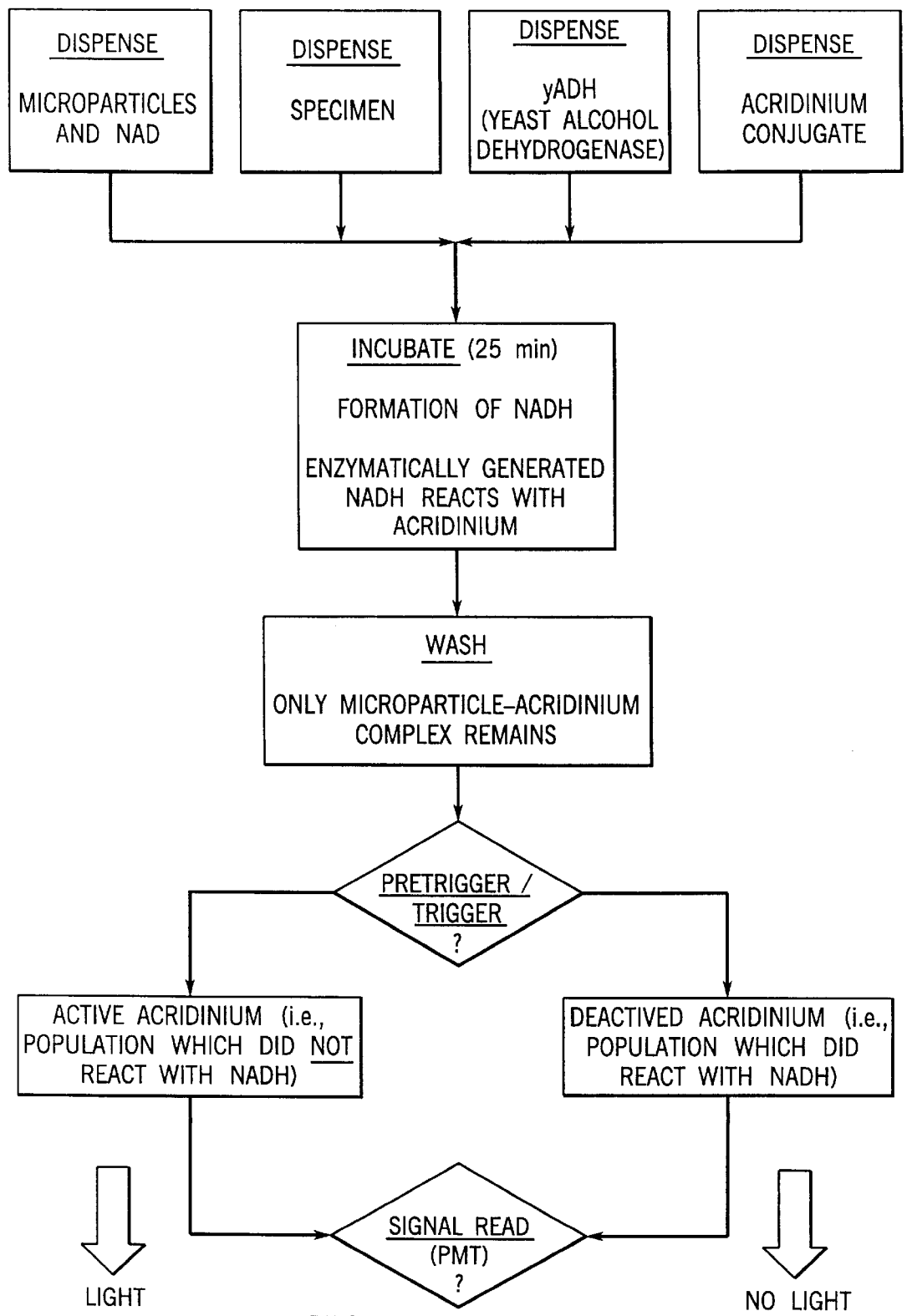
FIG. 15 is a flow chart illustrating an alternate procedure for an assay for ethanol.
Figure 16:
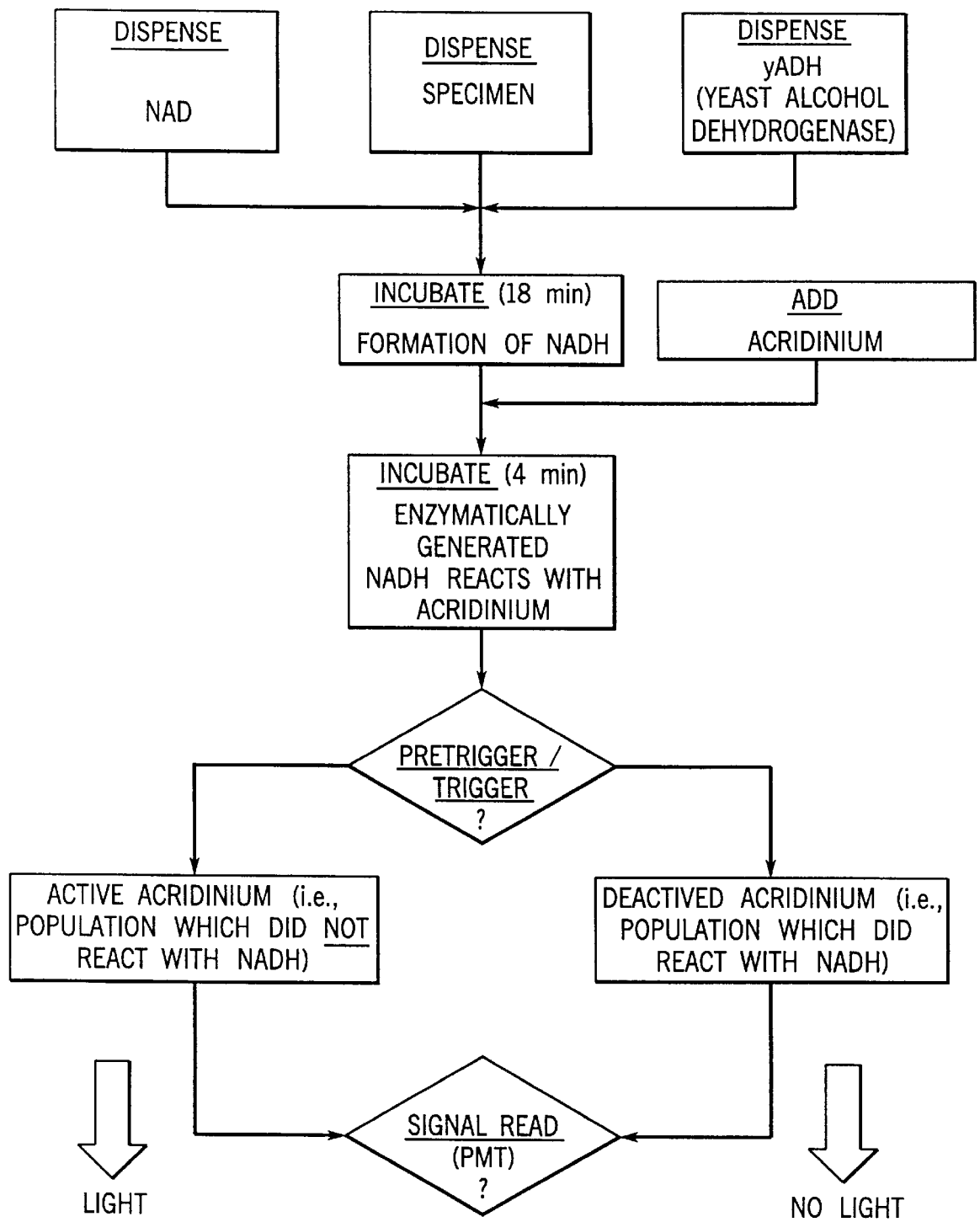
FIG. 16 is a flow chart illustrating an alternate procedure for an assay for ethanol.

This example illustrates a dose-response correlation for an ethanol assay. FIG. 13 is a flow chart illustrating the steps of the procedure employed in this example. FIG. 11 shows the signal as a function of ethanol concentration for an ethanol assay conducted via REA technology (diamond-shaped data points) and an ethanol assay conducted via the chemiluminescence technology of this invention (square-shaped data points and triangle-shaped data points). The data show that the assay of this invention can be more sensitive that the assay conducted via REA technology.

Figure 12:
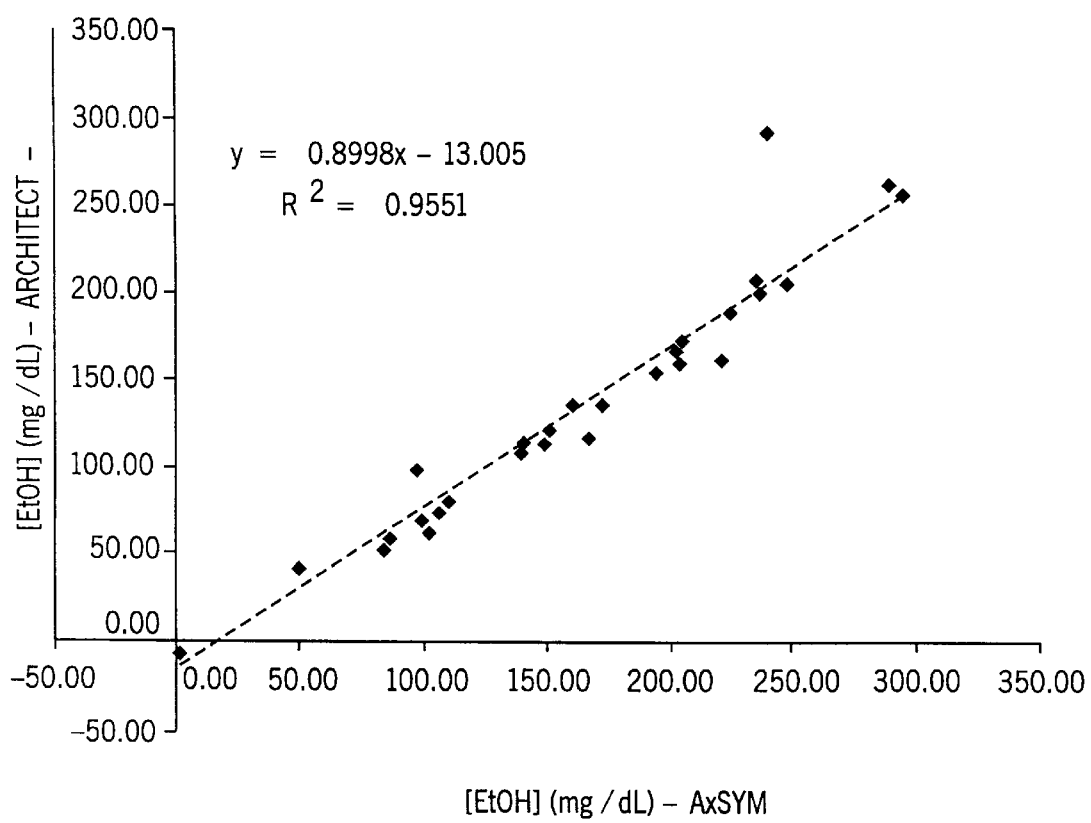
FIG. 12 is a graph illustrating the correlation between the concentration of ethanol determined by means of an REA assay and the concentration of ethanol determined by means of the assay of this invention.

This example illustrates that the concentration of ethanol determined by the method of this invention correlated well with the concentration of ethanol determined by REA technology. FIG. 12 shows that $R^2$ for the two different methods was 0.9551, which indicates excellent correlation.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining concentration of an analyte in a biological sample comprising the steps of:
   (a) combining the biological sample, at least one oxidizing enzyme for the analyte of interest, nicotinamide adenine dinucleotide, and a chemiluminescent label to form a reaction mixture;
   (b) allowing the analyte to undergo an oxidation-reduction reaction and nicotinamide adenine dinucleotide to be converted to the reduced form of nicotinamide adenine dinucleotide and further allowing the chemiluminescent label to react with the reduced form of nicotinamide adenine dinucleotide; and
   (c) determining the concentration of the analyte of interest in the biological sample by correlating the quantity of light emitted with the concentration of the reduced form of nicotinamide adenine dinucleotide.

2. The method of claim 1, wherein said chemiluminescent label is added to said reaction mixture subsequent to the commencing of the formation of the reduced form of nicotinamide adenine dinucleotide.

3. The method of claim 1, wherein said analyte is selected from the group consisting of ethanol, ethylene glycol, phenytoin, glucose, ketone bodies, triglycerides, cholesterol, lactate, α-amylase, ammonia, malate, androsterone, and testosterone.

4. The method of claim 1, wherein said analyte is ethanol.

5. The method of claim 1, further including the step of adding a trapping agent to the reaction mixture of step (a).

6. The method of claim 1, wherein said chemiluminescent label is a derivative of luminol or a derivative of acridine.

7. The method of claim 1, wherein said label is deactivated by reduction.

8. The method of claim 1, wherein said chemiluminescent label comprises an acridinium derivative.

9. The method of claim 1, wherein said chemiluminescent label comprises an acridinium conjugate.

10. The method of claim 1, wherein said reaction mixture is maintained at a pH equal to or greater than 9.

11. The method of claim 1, wherein a buffer is included in the reaction mixture.

12. The method of claim 1, wherein a pre-trigger is employed to condition the chemiluminescent label for reaction with alkaline peroxide.

13. The method of claim 1, wherein a trigger is employed to cause the chemiluminescent label to react with a nucleophile, thereby allowing the formation of a compound that emits light.

14. The method of claim 11, wherein the trigger is alkaline peroxide.

15. A method for determining concentration of an analyte in a biological sample comprising the steps of:
   (a) combining the biological sample, a solid phase, at least one oxidizing enzyme for the analyte of interest, nicotinamide adenine dinucleotide, and a chemiluminescent label to form a reaction mixture;
   (b) allowing the analyte to undergo an oxidation-reduction reaction and nicotinamide adenine dinucleotide to be converted to the reduced form of nicotinamide adenine dinucleotide and further allowing the chemiluminescent label to react with the reduced form of nicotinamide adenine dinucleotide;
   (c) separating the chemiluminescent label from the solid phase; and
   (d) determining the concentration of the analyte in the biological sample by correlating quantity of light emitted with the concentration of the reduced form of nicotinamide adenine dinucleotide.

16. The method of claim 15, wherein said chemiluminescent label is added to said reaction mixture subsequent to the commencing of the formation of the reduced form of nicotinamide adenine dinucleotide.

17. The method of claim 15, wherein said analyte is selected from the group consisting of ethanol, ethylene glycol, phenytoin, glucose, ketone bodies, triglycerides, cholesterol, lactate, alpha-amylase, ammonia, malate, androsterone, and testosterone.

18. The method of claim 15, wherein said analyte is ethanol.

19. The method of claim 15, further including the step of adding a trapping agent to the reaction mixture of step (a).

20. The method of claim 15, wherein said chemiluminescent label is a derivative of luminol or a derivative of acridine.

21. The method of claim 15, wherein said label wherein said label is deactivated by reduction.

22. The method of claim 15, wherein said chemiluminescent label comprises an acridinium derivative.

23. The method of claim 15, wherein said chemiluminescent label comprises an acridinium conjugate.

24. The method of claim 15, wherein said reaction mixture is maintained at a pH equal to or greater than 9.

25. The method of claim 15, wherein a buffer is included in the reaction mixture.

26. The method of claim 15, wherein a pre-trigger wherein a pre-trigger is employed to condition the chemiluminescent label for reaction with alkaline peroxide.

27. The method of claim 15, wherein a trigger is employed to cause the chemiluminescent label to react with a nucleophile, thereby allowing the formation of a compound that emits light.

28. The method of claim 27, wherein said trigger is alkaline peroxide.

\* \* \* \* \*